US010058298B2

(12) United States Patent
Lee et al.

(10) Patent No.: US 10,058,298 B2
(45) Date of Patent: Aug. 28, 2018

(54) RADIOGRAPHIC SYSTEM AND CONTROL METHOD THEREOF

(71) Applicant: Samsung Electronics Co., Ltd., Suwon-si (KR)

(72) Inventors: Dong Jae Lee, Hwaseong-si (KR); Soo Sang Yang, Suwon-si (KR); Hyeon Min Lee, Gunpo-si (KR); Jeong Pil Lee, Suwon-si (KR); Woo Sup Han, Yongin-si (KR); Hyun Woong Hwang, Suwon-si (KR); Seung Hoon Shin, Seoul (KR); Do Hyeong Hwang, Gunpo-si (KR); Jong Beom Her, Seoul (KR)

(73) Assignee: Samsung Electronics Co., Ltd., Suwon-si (KR)

(*) Notice: Subject to any disclaimer, the term of this patent is extended or adjusted under 35 U.S.C. 154(b) by 580 days.

(21) Appl. No.: 14/523,571

(22) Filed: Oct. 24, 2014

(65) Prior Publication Data
US 2015/0043716 A1 Feb. 12, 2015

Related U.S. Application Data

(63) Continuation of application No. 14/279,859, filed on May 16, 2014, which is a continuation-in-part of (Continued)

(30) Foreign Application Priority Data

Oct. 6, 2010 (KR) .................. 10-2010-0097304

(51) Int. Cl.
*A61B 6/00* (2006.01)
*G01L 5/22* (2006.01)
(Continued)

(52) U.S. Cl.
CPC ............ *A61B 6/462* (2013.01); *A61B 6/4452* (2013.01); *A61B 6/4464* (2013.01);
(Continued)

(58) Field of Classification Search
CPC ....... A61B 6/44; A61B 6/4405; A61B 6/4464; A61B 6/4476; A61B 6/4482; A61B 6/46;
(Continued)

(56) References Cited

U.S. PATENT DOCUMENTS

| 4,107,590 A | 8/1978 | Pury et al. |
| 4,163,929 A | 8/1979 | Janu et al. |

(Continued)

FOREIGN PATENT DOCUMENTS

| CN | 1334772 A | 2/2002 |
| CN | 1929785 A | 3/2007 |

(Continued)

OTHER PUBLICATIONS

Chinese Office Action dated Nov. 27, 2014, in counterpart Chinese Application No. 201110302134.5 (25 pages, in Chinese, including complete English translation).

(Continued)

Primary Examiner — Thomas R Artman
(74) Attorney, Agent, or Firm — NSIP Law

(57) ABSTRACT

A radiographic system includes a photographic unit; an operating panel including a button configured to be pressed to indicate that a movement direction of the photographic unit is to be limited to a specific movement direction; a measurement unit provided between the operating panel and the photographic unit and configured to measure a magnitude and a direction of an external force applied to the operating panel; and a drive unit configured to move the photographic unit only in the specific movement direction based on the magnitude and the direction of the external force measured by the measurement unit in response to the button being pressed.

18 Claims, 24 Drawing Sheets

Related U.S. Application Data application No. 13/738,221, filed on Jan. 10, 2013, now Pat. No. 8,755,492, which is a continuation-in-part of application No. 13/237,219, filed on Sep. 20, 2011, now Pat. No. 8,651,740.

(51) Int. Cl.
 *A61B 6/04* (2006.01)
 *A61B 6/10* (2006.01)

(52) U.S. Cl.
 CPC .......... *A61B 6/4476* (2013.01); *A61B 6/4482* (2013.01); *A61B 6/469* (2013.01); *A61B 6/547* (2013.01); *G01L 5/22* (2013.01); *A61B 6/0407* (2013.01); *A61B 6/102* (2013.01); *A61B 6/467* (2013.01)

(58) Field of Classification Search
 CPC ......... A61B 6/461; A61B 6/462; A61B 6/463; A61B 6/465; A61B 6/467
 See application file for complete search history.

(56) References Cited

U.S. PATENT DOCUMENTS

| | | | |
|---|---|---|---|
| 4,674,107 A | 6/1987 | Urban et al. | |
| 4,697,661 A | 10/1987 | Pajerski et al. | |
| 4,926,455 A | 5/1990 | Stojkov et al. | |
| 5,351,282 A | 9/1994 | Kadowaki et al. | |
| 5,416,819 A | 5/1995 | Uzuyama et al. | |
| 5,572,567 A | 11/1996 | Khutoryansky et al. | |
| 5,768,336 A | 6/1998 | Khutoryansky et al. | |
| 6,422,747 B2 | 7/2002 | Akutsu et al. | |
| 6,851,851 B2 | 2/2005 | Smith et al. | |
| 6,871,715 B1 | 3/2005 | Diaz Carmena et al. | |
| 7,177,393 B2 | 2/2007 | Kanemitsu | |
| 7,329,046 B1* | 2/2008 | Muszak | A61B 6/4441 378/196 |
| 7,534,037 B2 | 5/2009 | Curtis | |
| 7,597,473 B2 | 10/2009 | Graumann et al. | |
| 7,809,102 B2 | 10/2010 | Brada et al. | |
| 8,201,999 B2 | 6/2012 | Uchida et al. | |
| 8,419,276 B2* | 4/2013 | Oda | A61B 6/4283 378/198 |
| 8,553,842 B2 | 10/2013 | Moon et al. | |
| 8,651,740 B2 | 2/2014 | Yang et al. | |
| 8,755,492 B2 | 6/2014 | Lee et al. | |
| 8,848,865 B2* | 9/2014 | Nakayama | A61B 6/0414 378/37 |
| 9,149,247 B2* | 10/2015 | Lee | A61B 6/4452 |
| 9,532,763 B2* | 1/2017 | Lee | A61B 6/4452 |
| 9,675,308 B2 | 6/2017 | Yang et al. | |
| 9,687,205 B2 | 6/2017 | Lee et al. | |
| 9,757,080 B2* | 9/2017 | Lee | A61B 6/462 |
| 2002/0080921 A1 | 6/2002 | Smith et al. | |
| 2006/0120512 A1* | 6/2006 | Watanabe | A61B 6/10 378/198 |
| 2006/0126795 A1* | 6/2006 | Lumma | A61B 6/105 378/193 |
| 2007/0112458 A1 | 5/2007 | Kondo et al. | |
| 2008/0025469 A1* | 1/2008 | Watanabe | A61B 6/10 378/198 |
| 2009/0285355 A1 | 11/2009 | Brada et al. | |
| 2010/0215152 A1* | 8/2010 | Takahashi | A61B 6/4429 378/197 |
| 2010/0243924 A1 | 9/2010 | Uchida et al. | |
| 2010/0329426 A1* | 12/2010 | Oda | A61B 6/4283 378/98.2 |
| 2012/0087479 A1 | 4/2012 | Moon et al. | |
| 2012/0087480 A1 | 4/2012 | Yang et al. | |
| 2012/0155616 A1 | 6/2012 | Rijken et al. | |
| 2012/0277625 A1* | 11/2012 | Nakayama | A61B 6/0414 600/567 |
| 2013/0121477 A1 | 5/2013 | Lee et al. | |
| 2013/0343523 A1* | 12/2013 | Lee | A61B 6/4452 378/63 |
| 2014/0119516 A1 | 5/2014 | Yang et al. | |
| 2014/0321621 A1 | 10/2014 | Lee et al. | |
| 2014/0328456 A1* | 11/2014 | Lee | A61B 6/4452 378/28 |
| 2015/0012168 A1 | 1/2015 | Kuklish et al. | |
| 2015/0043716 A1* | 2/2015 | Lee | A61B 6/4452 378/98.2 |
| 2015/0313561 A1* | 11/2015 | Kwak | A61B 6/547 378/197 |
| 2015/0351711 A1* | 12/2015 | Lee | A61B 6/4452 378/62 |
| 2016/0220215 A1* | 8/2016 | Kwak | A61B 6/54 |

FOREIGN PATENT DOCUMENTS

| | | |
|---|---|---|
| CN | 102551747 A | 7/2012 |
| CN | 102949196 A | 3/2013 |
| EP | 1 642 693 A1 | 4/2006 |
| JP | 9-220220 A | 8/1997 |
| JP | H-11-324 A | 1/1999 |
| JP | 2003-81598 A | 3/2003 |
| JP | 2005-237613 A | 9/2005 |
| JP | 2010-227290 A | 10/2010 |
| JP | 2011-30699 A | 2/2011 |
| KR | 10-2012-0036562 A | 4/2012 |
| WO | WO 2009/136452 A1 | 11/2009 |
| WO | WO 2011/030255 A1 | 3/2011 |

OTHER PUBLICATIONS

International Search Report dated Jul. 27, 2015, in counterpart of International Application No. PCT/KR2015/004018, 3 pages in English.

Chinese Office Action dated Aug. 6, 2015, in the corresponding Chinese Patent Application No. 201110302134.5, 2 pages in Chinese, 2 Pages in English.

Korean Notice of Allowance dated Jun. 28, 2016 in counterpart Korean Application No. 10-2010-0097304. (7 pages with partial English translation).

Chinese Office Action dated Jan. 19, 2017, in counterpart Chinese Application No. 201510252782.2 (13 pages, in Chinese, including complete English translation).

Korean Office Action dated Jun. 24, 2013, in counterpart Korean Application No. 10-2010-0097304 (16 pages, including complete English translation translated by Google Translate).

Chinese Office Action dated Apr. 3, 2014, in counterpart Chinese Patent Application No. 201110302134.5 (8 pages, in Chinese, no English translation).

U.S. Appl. No. 14/150,760, filed Jan. 8, 2014, Soo-Sang Yang et al., Samsung Electronics Co., Ltd.

U.S. Appl. No. 14/264,500, filed Apr. 29, 2014, Dong Jae Lee et al., Samsung Electronics Co., Ltd.

U.S. Appl. No. 14/279,859, filed May 16, 2014, Dong Jae Lee et al., Samsung Electronics Co., Ltd.

Chinese Office Action dated Sep. 12, 2017 in corresponding Chinese Patent Application No. 201510252782.2 (14 pages in English and 10 pages in Chinese).

European Search Report dated Dec. 13, 2017 in corresponding European Patent Application No. 15786291.3 (12 pages in English).

Chinese Office Action dated Apr. 10, 2018 in corresponding Chinese Patent Application No. 201510252782.2 (22 pages in English and 16 pages in Chinese).

Extended European Search dated May 18, 2018 in corresponding European Patent Application No. 15786291.3 (12 pages in English).

U.S. Office Action dated Jun. 26, 2018, in related U.S. Appl. No. 15/620,147 (20 pages in English, copies of forms PTO-892 and PTO-1449 omitted).

* cited by examiner

RADIOGRAPHIC SYSTEM AND CONTROL METHOD THEREOF

CROSS-REFERENCE TO RELATED APPLICATIONS

This application is a continuation of application Ser. No. 14/279,859 filed on May 16, 2014, now U.S. Pat. No. 9,757,080 issued on Sep. 12, 2017, which is a continuation-in-part of application Ser. No. 13/738,221 filed on Jan. 10, 2013, now U.S. Pat. No. 8,755,492 issued on Jun. 17, 2014, which is a continuation-in-part of application Ser. No. 13/237,219 filed on Sep. 20, 2011, now U.S. Pat. No. 8,651,740 issued on Feb. 18, 2014. This application claims the benefit of Korean Patent Application No. 10-2010-0097304 filed on Oct. 6, 2010, in the Korean Intellectual Property Office. The disclosures of application Ser. Nos. 13/738,221 and 13/237,219 and Korean Patent Application No. 10-2010-0097304 are incorporated herein by reference in their entirety for all purposes.

BACKGROUND

1. Field

This application relates to a radiographic system that can be moved by an operator using a reduced force and a control method thereof.

2. Description of Related Art

A radiographic system is designed to obtain an internal image of a human body using X-rays. The radiographic system is used to inspect injuries of an internal part or diseases of the human body that are not easily checked by the external appearance of the human body.

The radiographic system obtains an internal image of the human body by radiating X-rays to a desired region to be photographed (imaged), such as a head part and a chest part of the human body, and by detecting X-rays transmitted through the region.

The radiographic system is provided with an X-ray tube to radiate X-rays to a desired region. The X-ray tube is mounted to be movable to inspect various regions of the human body.

In general, a ceiling type radiographic system is provided with at least one guide rail installed on the ceiling of an inspection room, and a telescoping post frame mounted on the guide rail. The X-ray tube is rotatably installed on a lower end of the telescoping post frame.

In recent years, the ceiling type radiographic system has been provided with an automatic movement mode by installing an actuator on an axis of movement of the ceiling type radiographic system, and as an operator inputs a desired position, the X-ray tube automatically moves to the position input by the operator.

In addition, the radiographic system may have a manual movement mode for the operator to manually move the X-ray tube. A manual operating switch is provided near the X-ray tube, and the operator may manually move the X-ray tube after switching the operation mode from the automatic movement mode to the manual movement mode using the manual operating switch.

Due to the weight of the X-ray tube and the frictional resistance of the moving parts of the radiographic system, the operator needs to apply a large force or torque to the X-ray tube to move the X-ray tube in the manual movement mode. Accordingly, when there is a need for a repetitive movement of the X-ray tube, the operator may experience physical fatigue.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a radiographic system includes a photographic unit; an operating panel including a button configured to be pressed to indicate that a movement direction of the photographic unit is to be limited to a specific movement direction; a measurement unit provided between the operating panel and the photographic unit and configured to measure a magnitude and a direction of an external force applied to the operating panel; and a drive unit configured to move the photographic unit only in the specific movement direction based on the magnitude and the direction of the external force measured by the measurement unit in response to the button being pressed.

The drive unit may be further configured to output power for moving the photographic unit only in the specific movement direction based on the magnitude of the external force measured by the measurement unit in response to the button being pressed.

The drive unit may be further configured to move the photographic unit only in the specific movement direction only while the button is pressed, and stop the movement of the photographic unit in response to the pressed button being released.

In another general aspect, a radiographic system includes a photographic unit; an operating panel configured to receive an input of radiographic information for driving the photographic unit; a measurement unit provided between the photographic unit and the operating panel and configured to measure a magnitude and a direction of an external force applied to the operating panel; and a system control unit configured to convert a coordinate system of the measurement unit to a coordinate system of the radiographic system based on a rotation angle of the photographic unit.

The measurement unit may be further configured to measure the direction of the external force in the coordinate system of the measurement unit; and the system control unit may be further configured to convert the direction of the external force measured by the measurement unit in the coordinate system of the measurement unit to a direction in the coordinate system of the radiographic system based on the rotation angle of the photographic unit.

The radiographic system may further include a drive unit configured to move the photographic unit based on the magnitude of the external force measured by the measurement unit in the converted direction of the coordinate system of the radiographic system.

The radiographic system may further include a potentiometer or encoder configured to detect the rotation angle of the photographic unit, and provide information on the detected rotation angle of the photographic unit to the system control unit.

In another general aspect, a radiographic system includes a photographic unit; a system control unit configured to calculate a resonance frequency of the radiographic system at a movement position of the photographic unit, and output a control signal from which a frequency band including the calculated resonance frequency has been removed; and a drive unit configured to move the photographic unit according to the control signal output from the system control unit.

The system control unit may be further configured to store resonance frequency information of the radiographic system at predetermined movement positions of the photographic unit, and calculate the resonance frequency of the radiographic system at the movement position of the photographic unit based on the stored resonance frequency information.

The system control unit may be further configured to store coordinates of predetermined points in a movement space of the photographic unit and resonance frequency information of the radiographic system at the predetermined points, and calculate the resonance frequency of the radiographic system at the movement position of the photographic unit by interpolating the stored resonance frequency information of the radiographic system at ones of the predetermined points that are closest to the movement position of the photographic unit.

In another general aspect, a radiographic system includes a photographic unit; a speed sensor configured to detect a moving speed of the photographic unit; and a system control unit configured to stop movement of the photographic unit at a preset stop position in response to the moving speed of the photographic unit being less than or equal to a first reference speed at the preset stop position.

The system control unit may be further configured to decrease the moving speed of the photographic unit so that the movement of the photographic unit stops at the preset stop position in response to the photographic unit being within a preset distance of the preset stop position and the moving speed of the photographic unit being less than or equal to the first reference speed.

The radiographic system may further include a drive unit configured to move the photographic unit; and the system control unit may be further configured to control the drive unit to stop operating to stop the movement of the photographic unit at the preset stop position in response to the moving speed of the photographic unit being less than or equal to the first reference speed at the preset stop position.

The system control unit may be further configured to control the drive unit to decrease a driving speed of the photographic unit so that the movement of the photographic unit stops at the present stop position in response to the photographic unit being within a preset distance of the present stop position and the moving speed of the photographic unit being less than or equal to the first reference speed.

The radiographic system may further include an operating panel including an input unit configured to instruct the system control unit to stop the movement of the photographic unit at the preset stop position.

In another general aspect, a radiographic system includes a photographic unit; a speed sensor configured to detect a moving speed of the photographic unit; and a system control unit configured to change a ratio of the moving speed of the photographic unit to a force applied to the photographic unit according to a change in the moving speed of the photographic unit in response to the moving speed of the photographic unit being less than or equal to a second reference speed.

The system control unit may be further configured to maintain constant the ratio of the moving speed of the photographic unit to the force applied to the photographic unit in response to the moving speed of the photographic unit being greater than the second reference speed.

The system control unit may be further configured to reduce the ratio of the moving speed of the photographic unit to the force applied to the photographic unit in response to the moving speed of the photographic unit being less than or equal to the second reference speed.

The radiographic system may further include a measurement unit configured to measure a magnitude and a direction of an external force applied to the photographic unit; and a drive unit configured to move the photographic unit based on the magnitude and the direction of the external force measured by the measurement unit and the ratio of the moving speed of the photographic unit to the force applied to the photographic unit; wherein the system control unit may be further configured to reduce the ratio of the moving speed of the photographic unit to the force applied to the photographic unit as the moving speed of the photographic unit decreases in response to the moving speed of the photographic unit being less or equal to the second reference speed, thereby causing the drive unit to reduce a driving force for moving the photographic unit as the moving speed of the photographic unit decreases in response to the moving speed of the photographic unit being less or equal to the second reference speed.

The radiographic system may further include an operating panel including an input unit configured to instruct the system control unit to change the ratio of the moving speed of the photographic unit to the force applied to the photographic unit in response to the moving speed being less than or equal to the second reference speed.

Other features and aspects will be apparent from the following detailed description, the drawings, and the claims.

DETAILED DESCRIPTION

Figure 1:
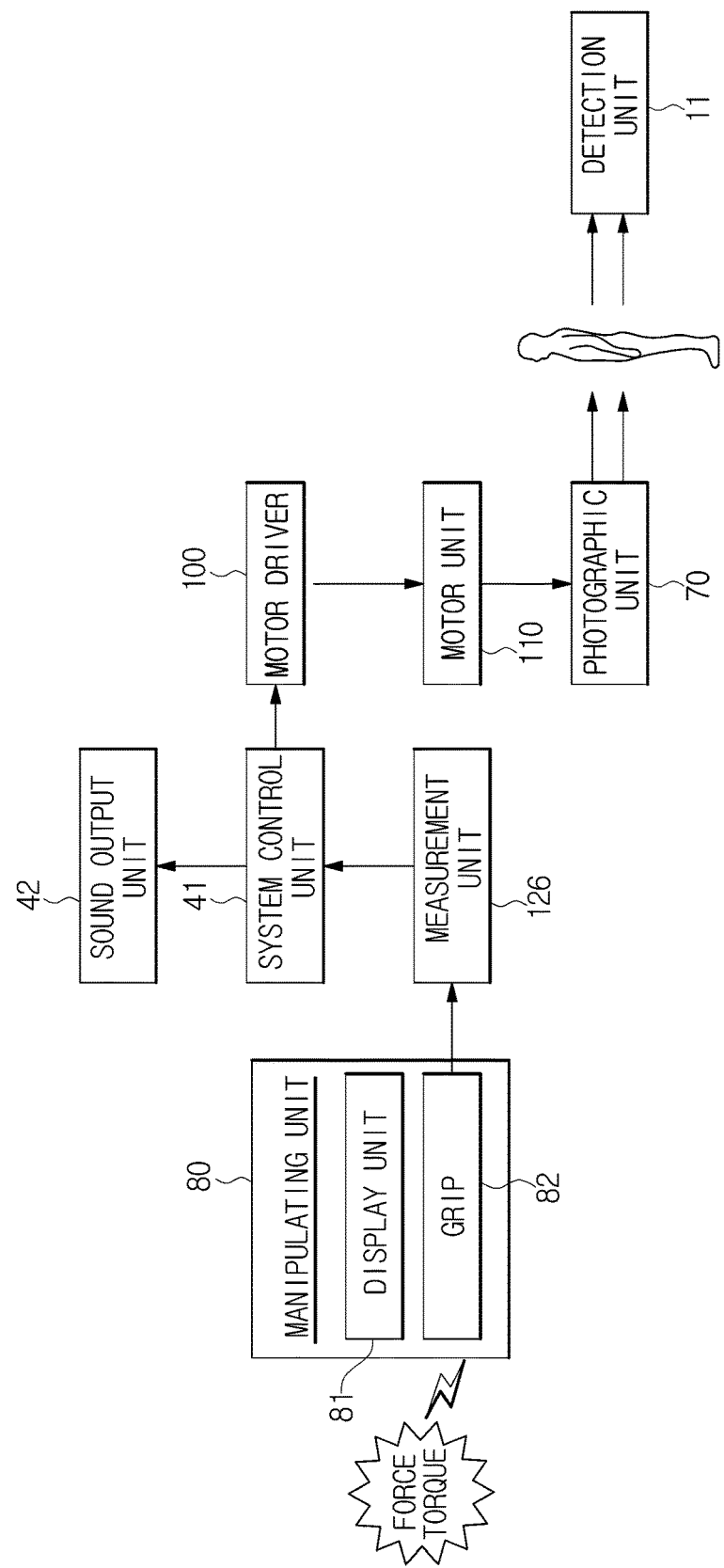
FIG. 1 is a block diagram illustrating the configuration of a radiographic system in accordance with one example.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

Figure 2:
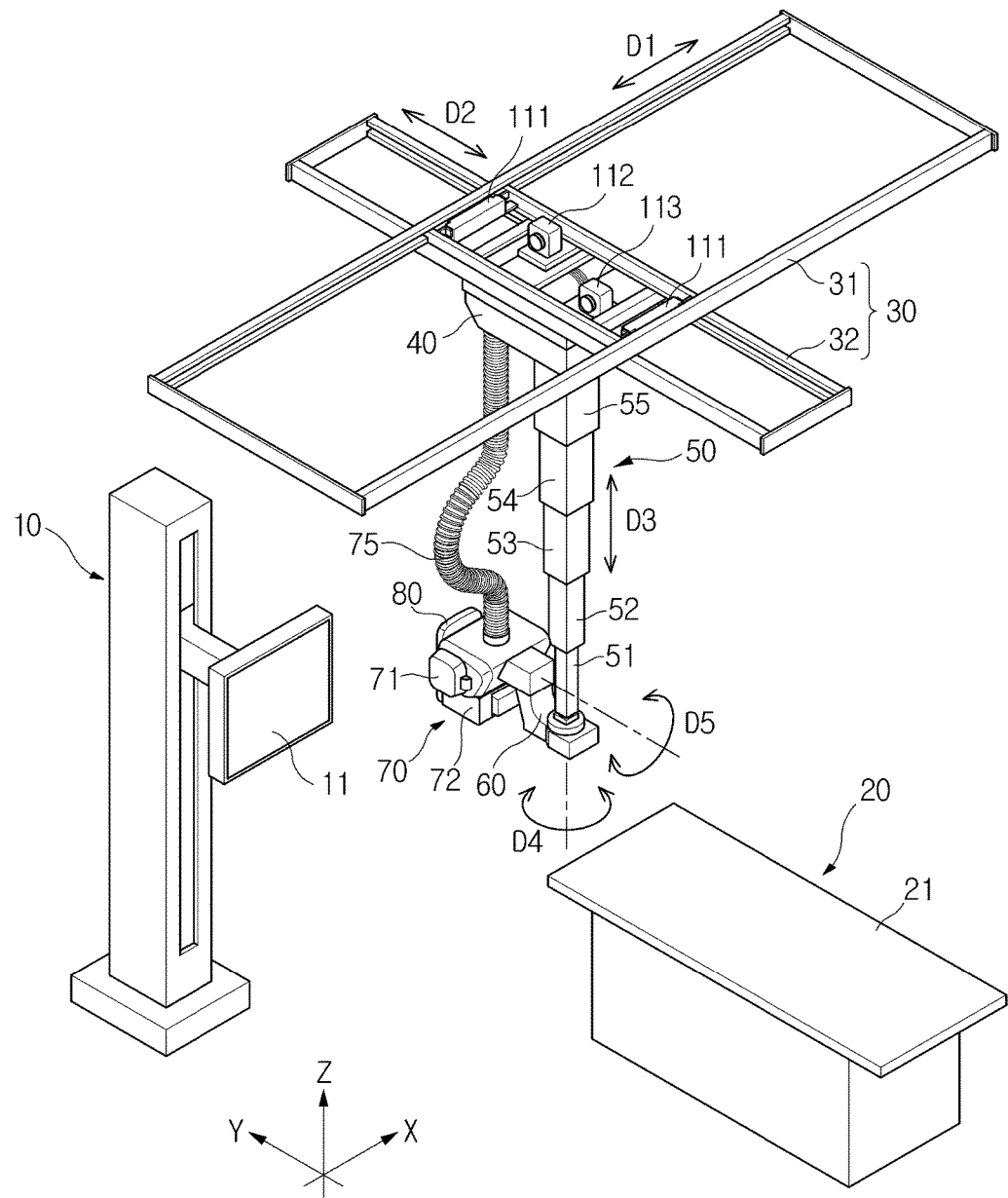
FIG. 2 is a perspective view illustrating the configuration of the radiographic system of FIG. 1 in accordance with one example.
Figure 3:
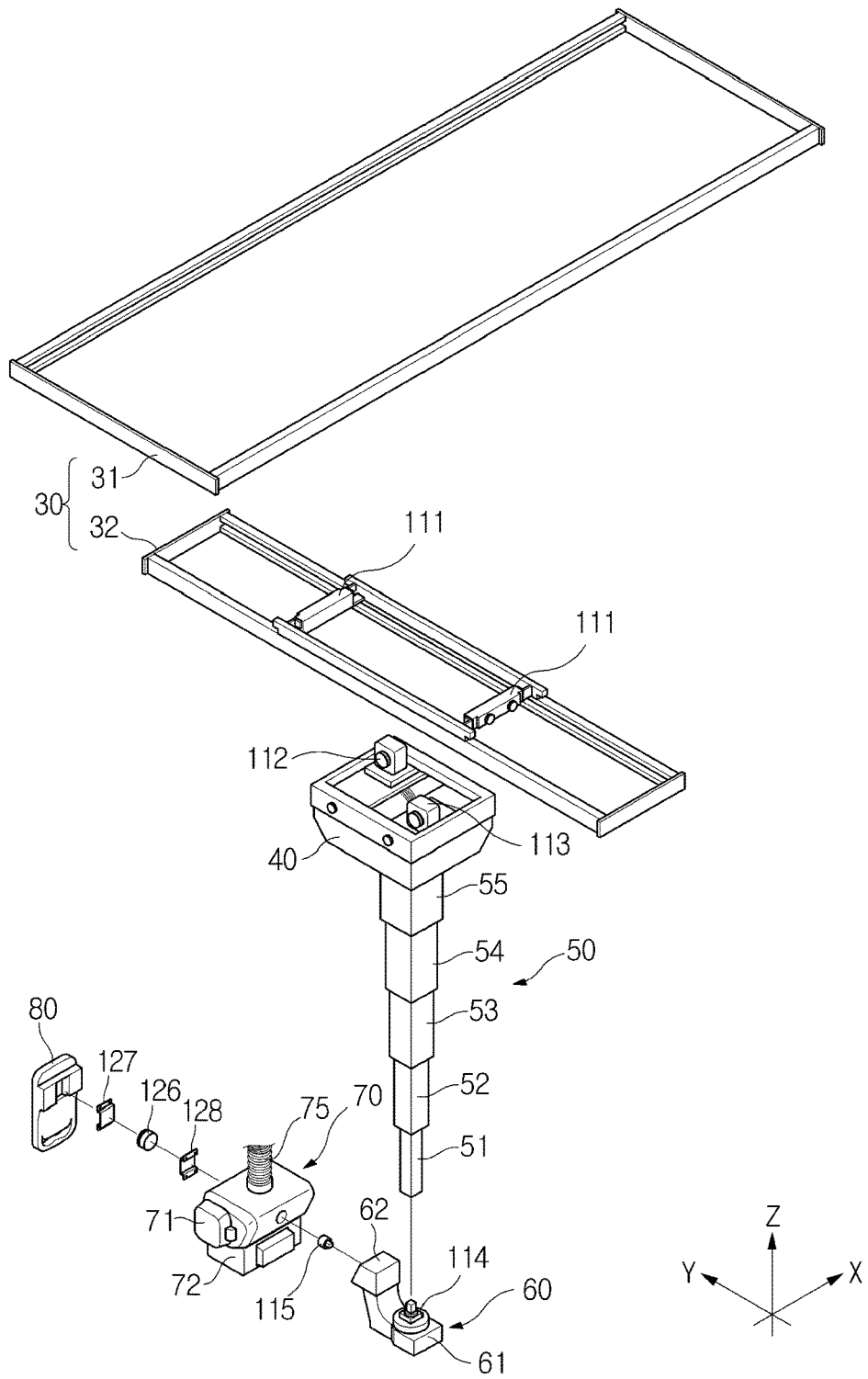
FIG. 3 is an exploded perspective view illustrating the configuration of a portion of the radiographic system of FIGS. 1 and 2 in accordance with one example.
Figure 4:
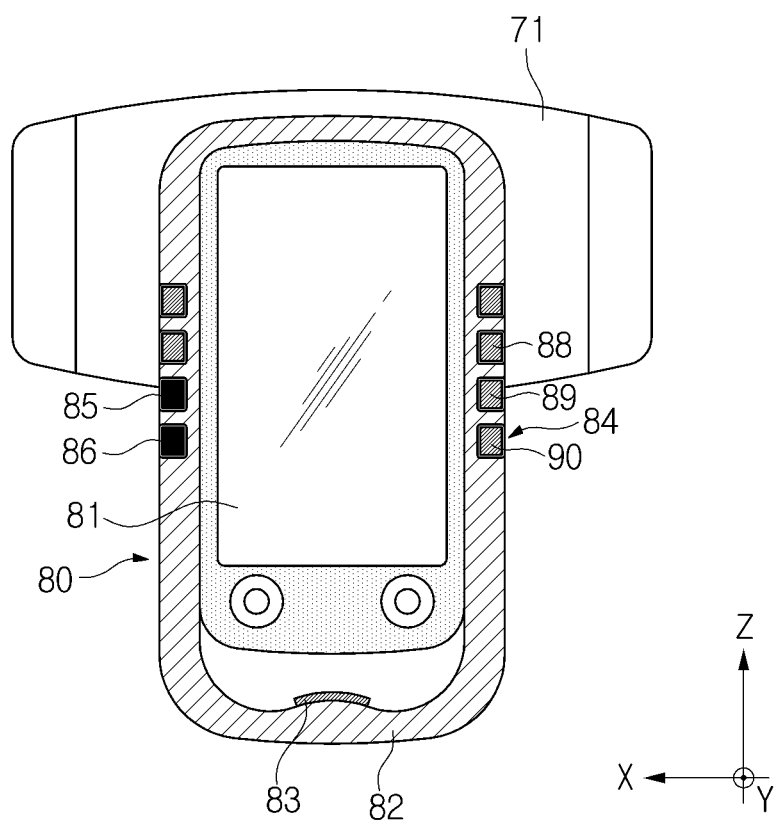
FIG. 4 is a front view illustrating a manipulating unit of the radiographic system of FIGS. 1-3 in accordance with one example.
Figure 11:
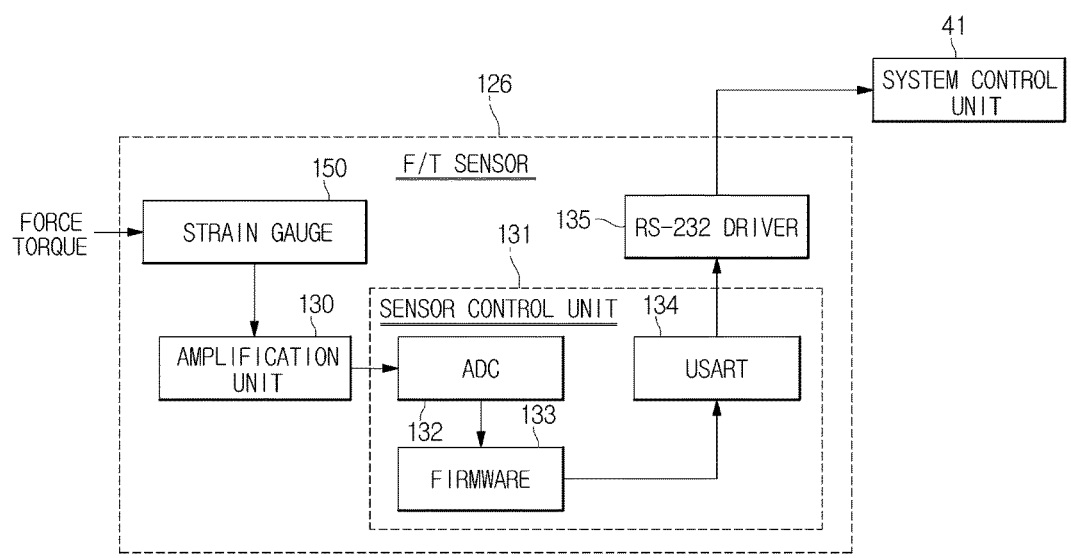
FIG. 11 is a block diagram illustrating the force/torque sensor of FIGS. 6-10 in accordance with one example.
Figure 12:
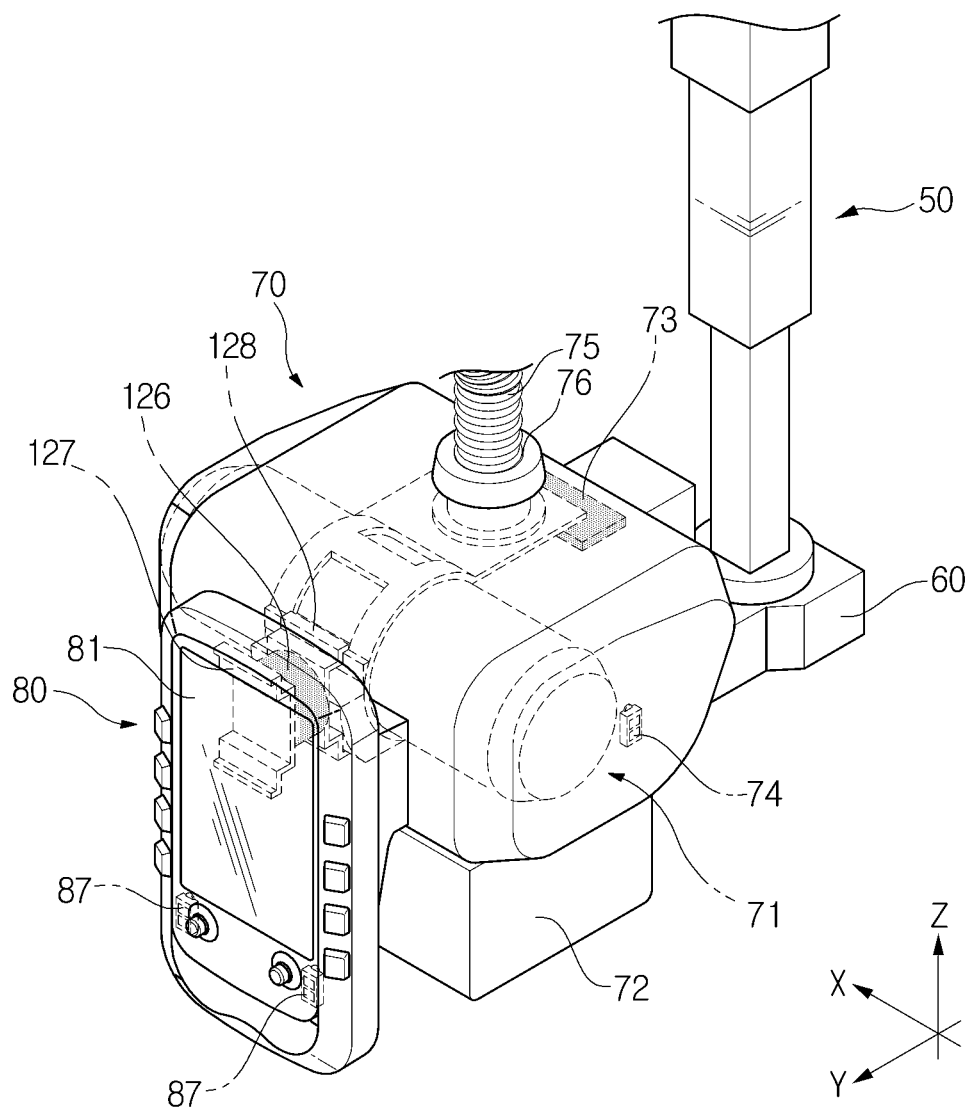
FIG. 12 is a perspective view illustrating the internal structure of the manipulating unit, a measurement unit, and a photographic unit of the radiographic system of FIGS. 1-11 in accordance with one example.
Figure 13:
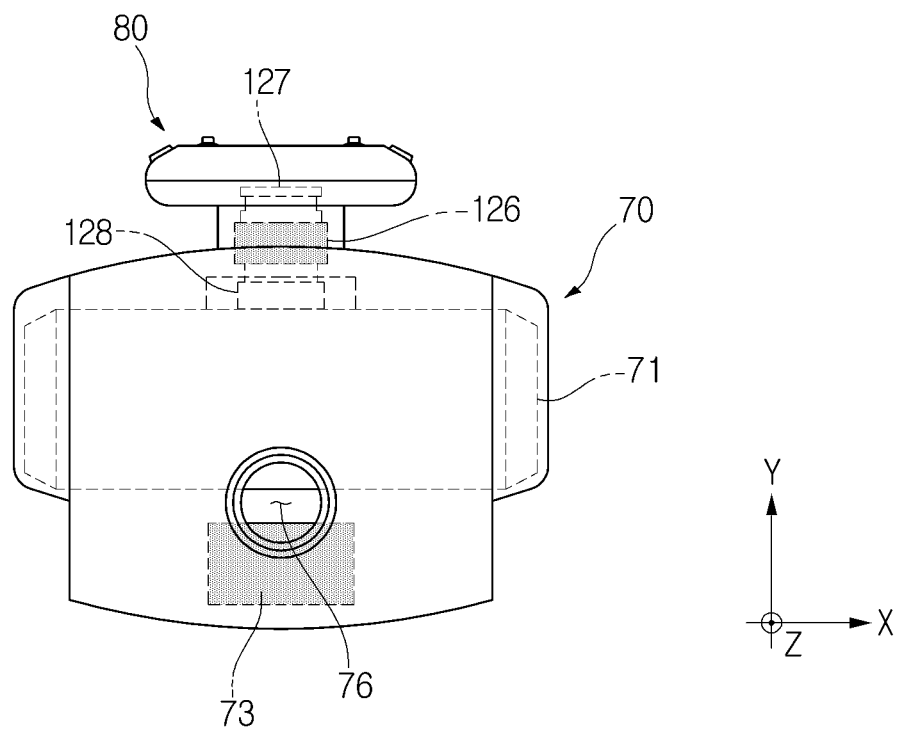
FIG. 13 is a top view illustrating the manipulating unit, the measurement unit, and the photographic unit of FIG. 12 in accordance with one example.

FIG. 1 is a block diagram illustrating the configuration of a radiographic system in accordance with one example. FIG. 2 is a perspective view illustrating the configuration of the radiographic system of FIG. 1 in accordance with one example. FIG. 3 is an exploded perspective view illustrating the configuration of a portion of the radiographic system of FIGS. 1 and 2 in accordance with one example. FIG. 4 is a front view illustrating a manipulating unit of the radiographic system of FIGS. 1-3 in accordance with one example. FIG. 12 is a perspective view illustrating the internal structure of the manipulating unit, a measurement unit, and a photographic unit of the radiographic system of FIGS. 1-11 in accordance with one example. FIG. 13 is a top view illustrating the manipulating unit, the measurement unit, and the photographic unit of FIG. 12 in accordance with one example.

Referring to FIG. 1, a radiographic system includes a manipulating unit 80 that is configured to provide an interface for manipulation of the radiographic system, and includes a display unit 81 configured to provide an interface through which information related to X-ray imaging is input and each part of the radiographic system is manipulated, and a grip 82 configured to be gripped by an operator to manually manipulate the radiographic system, a measurement unit 126 (sensor unit) configured to measure (to sense) a force or a torque applied to a photographic unit 70 (which may also be referred to as an X-ray source unit) through the grip 82 of the manipulating unit 80, a system control unit 41 configured to generate a control signal to move the photographic unit 70 based on a measurement result of the measurement unit 126, a motor driver 100 configured to drive a motor unit 110 according to the control signal of the system control unit 41, the motor unit 110 being configured to apply a driving force to move the photographic unit 70, the photographic unit 70 being configured to photograph an object, such as a patient, by radiating X-rays to the object, and a detection unit 11 (X-ray detection unit) configured to detect X-rays transmitted through the object. The system control unit 41 outputs an alarm sound indicating movement of the photographic unit 70 through a sound output unit 42, thereby notifying the operator that the movement of the photographic unit 70 is being performed with the assistance of the motor unit 110. Each part of the radiographic system will be described in detail below with reference to FIGS. 2 to 4.

Referring to FIGS. 2 and 3, the radiographic system includes a guide rail unit 30, a moving carriage 40 inside which the system control unit 41 is mounted, a telescoping post frame 50 (hereinafter referred to as simply the post frame 50), the motor unit 110, the photographic unit 70, the measurement unit 126, and the manipulating unit 80.

The radiographic system further includes a photographic stand 10 supporting the detection unit 11 configured to detect the X-rays transmitted through the object, and a photographic table 20 including a surface 21 configured to support an object to be photographed, such as a patient.

The guide rail unit 30, the moving carriage 40, and the post frame 50 enable the photographic unit 70 to be moved toward the object.

The guide rail unit 30 includes a first guide rail 31 and a second guide rail mounted at a predetermined angle with respect to each other. In the example of FIGS. 2 and 3, the first guide rail 31 extends in a direction perpendicular to a direction in which the second guide rail 32 extends.

The first guide rail 31 is mounted on a ceiling of an inspection room in which the radiographic system is installed.

The second guide rail 32 is disposed below the first guide rail 31, and is slidably mounted on the first guide rail 31. The second guide rail 32 is includes rollers (not shown) that are movable along the first guide rail 31.

The direction in which the first guide rail 31 extends is defined as a first direction D1, and the direction in which the second guide rail 32 extends is defined as a second direction D2. Accordingly, the first direction D1 and the second direction D2 are perpendicular to each other and are parallel to the ceiling of the inspection room.

The moving carriage 40 is disposed below the second guide rail 32, and is slidably mounted on the second guide rail 32. The moving carriage 40 includes rollers (not shown) that are movable along the second guide rail 32.

Accordingly, the moving carriage 40 is movable in the first direction D1 together with the second guide rail 32, and is also movable in the second direction D2 along the second guide rail 32. The system control unit 41 is mounted inside the moving carriage 40, and is configured to generate a control signal based on the measurement result of the measurement unit 126, and transmit the generated control signal to the motor driver 100.

The post frame 50 is disposed below the moving carriage 40 and is mounted on the moving carriage 40. The post frame 50 includes a plurality of posts 51, 52, 53, 54, and 55.

The plurality of posts 51, 52, 53, 54, and 55 form a telescoping structure that enables the length of the post frame 50 to be increased or decreased in a vertical direction in the inspection room while mounted on the moving carriage 40.

The direction in which the length of the post frame 50 increase or decreases is defined as a third direction D3. Accordingly, the third direction D3 is perpendicular to the first direction D1 and the second direction D2.

The photographic unit 70 is an apparatus configured to radiate X-rays to an object. The photographic unit 70 includes an X-ray tube 71 to generate X-rays, and a collimator 72 to guide the generated X-rays to the object. The photographic unit 70 may also be provided with a collision sensor 74 (not shown in FIGS. 1-3, but shown in FIG. 12). The illustration in FIG. 12 is merely an example of the collision sensor 74, and the position of the collision sensor 74 is not limited to the position shown in FIG. 12. Also, additional collision sensors 74 may be provided at other locations on the photographic unit 70, such as on the other side of the photographic unit 70 from the collision sensor 74 shown in FIG. 12, or on the other side of the photographic unit 70 from the manipulating unit 80. In one example, the collision sensor 74 is an optical sensor configured to sense an object in a moving direction of the photographic unit 70 and output a signal corresponding to a distance to the sensed object. The system control unit 41 is configured to control the motors 111, 112, and 113 to prevent the photographic unit 70 from colliding with the sensed object based on the signal output from the collision sensor 74.

A rotating joint unit 60 is disposed between the photographic unit 70 and the post frame 50. The rotating joint unit 60 couples the photographic unit 70 to the post frame 50 while supporting the load acting on the photographic unit 70.

The rotating joint unit 60 includes a first rotating joint 61 connected to a bottom post 51 of the post frame 50, and a second rotating joint 62 connected to the photographic unit 70.

The first rotating joint 61 is configured to be rotatable about a central axis of the post frame 50 that extends in the vertical direction in the inspection room. Accordingly, the first rotating joint 61 is rotatable in a plane that is perpendicular to the third direction D3. The rotating direction of the first rotating joint 61 is defined as a fourth direction D4, that is, a direction of rotation about an axis parallel to the third direction D3.

The second rotating joint 62 is configured to be rotatable in a plane that is perpendicular to the ceiling of the inspection room. Accordingly, the second rotating joint 62 is rotatable in a direction of rotation about an axis that may be parallel to the first direction D1 or the second direction D2, depending on a rotation of the first rotating joint 61 in the fourth direction D4. The rotating direction of the second rotating joint 62 is defined as a fifth direction D5, that is a direction of rotation about an axis that may extend parallel to the first direction D1 or the second direction D2, depending on a rotation of the first rotating joint 61 in the fourth direction D4.

Accordingly, the photographic unit 70 is rotatable in the fourth direction D4 and the fifth direction D5 while connected to the rotating joint unit 60, and is also movable in the first direction D1, the second direction D2, and the third direction D3 while connected to the post frame 50 through the rotating joint unit 60.

In order to move the photographic unit 70 in the first direction D1 to the fifth direction D5, the motor unit 110 is provided. The motor unit 110 may include a plurality of motors, each of which may be an electrical motor, and may include an encoder or a potentiometer configured to provide information on the speed and position of a shaft of the motor.

The motor unit 110 may be provided with a first motor 111, a second motor 112, a third motor 113, a fourth motor 114, and a fifth motor 115 respectively corresponding to the first to fifth directions D1 to D5. In the example in FIGS. 2 and 3, two motors 111 are provided.

For the convenience of design, the motors 111, 112, 113, 114 and, 115 may be disposed at various positions. For example, the first motors 111 configured to move the second guide rail 32 in the first direction D1 may be disposed at positions near the first guide rail 31, the second motor 112 configured to move the moving carriage 40 in the second direction D2 may be disposed at a position near the second guide rail 32, and the third motor 113 configured to increase or decrease the length of the post frame 50 in the third direction D3 may be disposed inside the moving carriage 40. In addition, the fourth motor 114 configured to rotate the photographic unit 70 in the fourth direction D4 may be disposed at a position near the first rotating joint 61, and the fifth motor 115 configured to rotate the photographic unit 70 in the fifth direction D5 may be disposed at a position near the second rotating joint 62.

Each motor of the motor unit 110 may be connected to a power transmission unit (not shown) to translate or rotate the photographic unit 70 in the first to fifth directions D1 to D5. The power transmission unit (not shown) may include a belt, a pulley, a chain, a sprocket, or any other element that is generally used as a power transmission unit.

The manipulating unit 80 is provided at one side of the photographic unit 70 to provide an interface through which various information related to X-ray imaging is input and each part of the radiographic system is manipulated.

Referring to FIG. 4, the manipulating unit 80 includes a display unit 81 to provide an interface through which information related to X-ray imaging is input and each part of the radiographic system is manipulated, and a grip 82 configured to be gripped by an operator to manually manipulate the radiographic system. In addition, a button unit 84 for manipulating the radiographic system is provided on the manipulating unit 80, and collision sensors 87 may be provided on the manipulating unit 80 as shown in FIG. 12. The illustration in FIG. 12 is merely an example of the collision sensors 87, and the positions of the collision sensors 87 are not limited to the positions shown in FIG. 12. Also, additional collision sensors 87 may be provided at other locations on the manipulating unit 80. In one example, the collision sensors 87 are optical sensors configured to sense an object in a moving direction of the photographic unit 70 and output a signal corresponding to a distance to the sensed object. The system control unit 41 is configured to control the motors 111, 112, and 113 to prevent the photographic unit 70 from colliding with the sensed object based on the signal output from the collision sensors 87. When the radiographic system images a subject, the display unit 81 of the manipulating unit 80 may provide a preview function of displaying a captured image or video to enable an operator to immediately view the captured image or video. The display unit 81 of the manipulating unit 80 as well as a workstation (not shown) may display the captured image or video, and therefore the operator may immediately view the captured image or video on either one or both of the workstation and the display unit 81 of the manipulating unit 80.

The display unit 81 includes a touch screen to which a touch gesture of the operator may be input. Soft key buttons for performing the same functions as all of the physical buttons of the button unit 84 may be implemented on the touch screen. The operator may input the same command input by manipulation of a physical button by touching the corresponding soft key button implemented on the touch screen. The button unit 84 includes a fourth direction rotation selecting button 85 and a fifth direction rotation selecting button 86 to be pressed by the operator when the operator desires to rotate the photographic unit 70 in the fourth direction or the fifth direction. That is, when the operator desires to rotate the photographic unit 70 in the fourth direction D4, the operator may rotate the photographic unit 70 after pressing the fourth direction rotation selecting button 85, or may rotate the photographic unit 70 while pressing the fourth direction rotation selecting button 85. When the operator desires to rotate the photographic unit 70 in the fifth direction D5, the operator may rotate the photographic unit 70 after pressing the fifth direction rotation selecting button 86, or may rotate the photographic unit 70 while pressing the fifth direction rotation selecting button 86. The illustration of the rotation selecting buttons 85 and 86 in FIG. 4 is merely an example, and the positions of the rotation selecting buttons 85 and 86 are not limited to the positions shown in FIG. 4. Soft key buttons for performing the same functions as the rotation selecting buttons 85 and 86 may be implemented on the touch screen.

Although the grip 82 is illustrated in FIG. 4 as being provided at a lower side of the manipulating unit 80, the position of the grip 82 is not limited to that position, and the grip 82 may be provided at a different position on the manipulating unit 80.

An operator may move and rotate the photographic unit 70 by gripping the grip 82 of the manipulating unit 80 to apply a force or a torque to the photographic unit 70. The movement and rotation of the photographic unit 70 in response to the force or torque applied by the operator will be described later.

The system control unit 41 is provided to control the devices provided in the radiographic system, including the motor driver 100 and the manipulating unit 80, and is electrically connected to the devices provided in the radiographic system. The system control unit 41 may be mounted inside the moving carriage 40.

The system control unit 41 is electrically connected to the motor driver 100 configured to drive each motor of the motor unit 110 to move the photographic unit 70 to a desired position.

For example, if the operator inputs a desired photographic position of the photographic unit 70 through the manipulating unit 80, the system control unit 41 determines a current position of the photographic unit 70 and the desired photographic position, and generates a control signal to control the operation of the motor unit 110 to move the photographic unit 70 to the desired photographic position, and outputs the generated control signal to the motor driver 100. The photographic unit 70 is moved to the desired photographic position by the operation of the motor 110. This mode of operation is referred to as an automatic movement mode. The automatic movement mode may be manipulated in a remote scheme through a remote controller including an interface that receives a command to move the photographic unit 70 to a desired position, or may be manipulated through the button unit 84 of the manipulating unit 80. Alternatively, the automatic movement mode may be manipulated through a workstation.

In addition, the operator may move the photographic unit 70 to a desired photographic position by directly applying a force or a torque to the photographic unit 70. This mode of operation is referred to as a manual movement mode. In order to convert from the automatic movement mode to the manual movement mode, a mode conversion unit 83 is provided. The mode conversion unit 83 may be mounted on the grip 82 of the manipulating unit 80 in the form of a switch. The operation mode is converted to the manual movement mode if the operator presses the mode conversion unit 83, and is converted to the automatic movement mode if the operator releases the mode conversion unit 83. Alternatively, the mode conversion unit 83 may be integrally formed with the grip 82. The operation mode is converted to the manual movement mode if the operator presses the mode conversion unit 83 by pressing the grip 82, and is converted to the automatic movement mode if the operator releases the mode conversion unit by releasing the grip 82. Alternatively, the operation mode may be converted to the manual movement mode without using the grip 82 if a force or a torque is detected by the measurement unit 126.

In the manual movement mode, a large force or a large torque must be applied to move the position of the photographic unit 70 since the frictional force generated by the motor unit 110 needs to be overcome. However, when the operator applies a force or a torque to the photographic unit 70, if the intention of the operator is recognized and the motor unit 110 is driven in response to the intention of the operator, the photographic unit 70 may be moved with a smaller force or torque than if the operator had to move the photographic unit 70 without the assistance of the motor unit 110. The manual movement mode in which the motor unit 110 is driven in response to the intention of the operator to move the photographic unit 70 may be referred to as a power-assisted movement mode or simply power-assisted mode to avoid confusion with a manual movement mode in which the user manually moves a photographic unit without a motor unit being driven.

Accordingly, in order to recognize the intention of the operator, the radiographic system is provided with the measurement unit 126 to measure the force or the torque being applied to the photographic unit 70 by the operator. A signal indicating the force or torque measured by the measurement unit 126 is transmitted to the system control unit 41, and the system control unit 41 operates the motor unit 110 in response to the force or the torque measured by the measurement unit 126. The measurement unit 126 may include a force/torque sensor, and hereinafter will be referred to interchangeably as a measurement unit 126 or a force/torque sensor 126.

Figure 6:
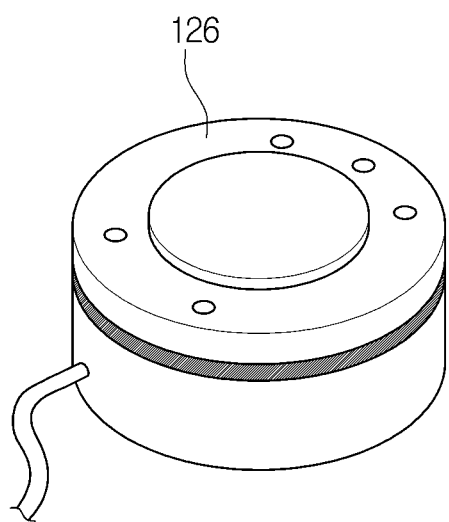
FIG. 6 is a perspective view illustrating a force/torque sensor of the radiographic system of FIGS. 1-3 in accordance with one example.
Figure 7:
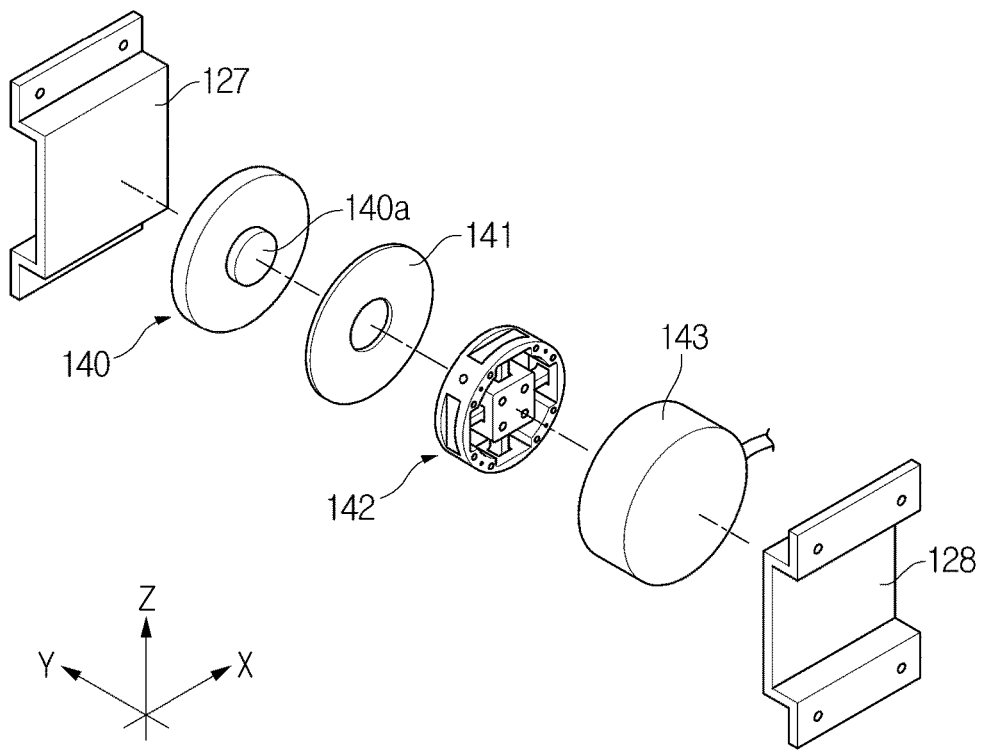
FIG. 7 is an exploded perspective view illustrating the force/torque sensor of FIG. 6 and brackets for mounting the force/torque sensor of FIG. 6 in accordance with one example.
Figure 8:
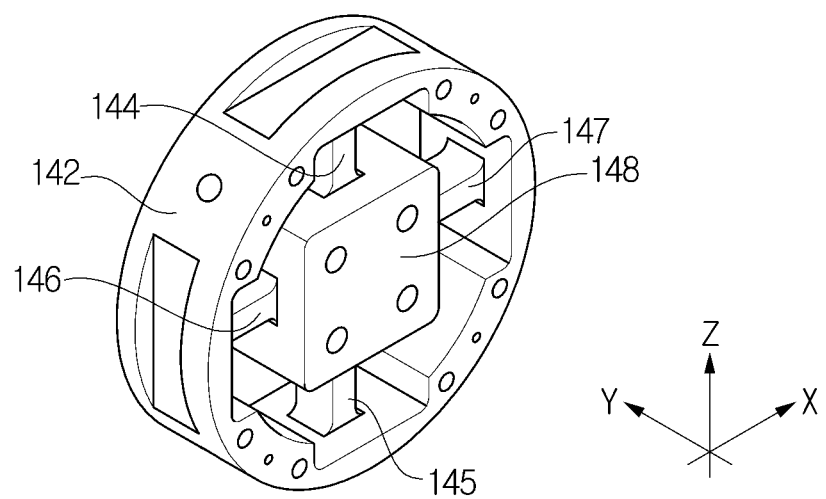
FIG. 8 is a perspective view illustrating a cross-shaped beam structure inside the force/torque sensor of FIGS. 6 and 7 in accordance with one example.
Figure 9:
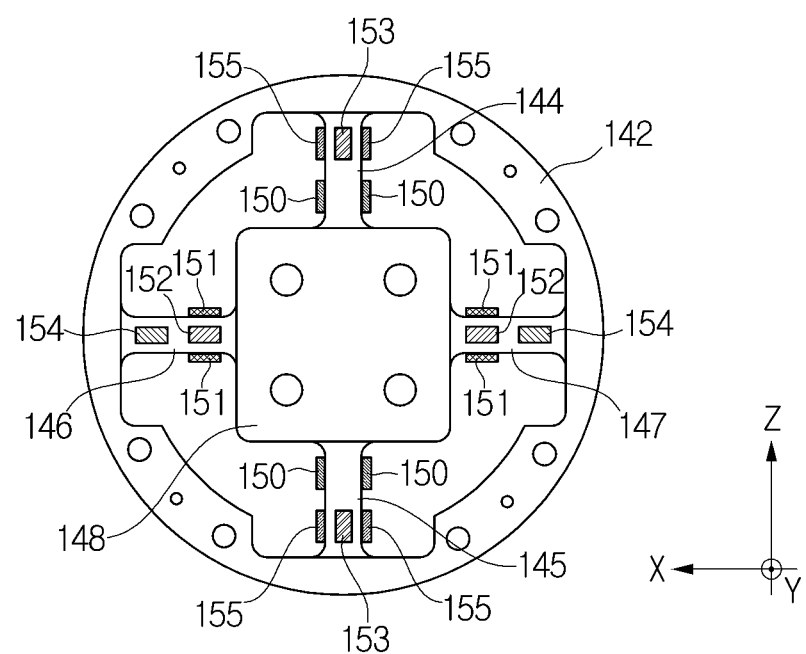
FIG. 9 is a front view illustrating the positions of strain gauges mounted on the cross-shaped beam structure of FIG. 8 in accordance with one example.
Figure 10:
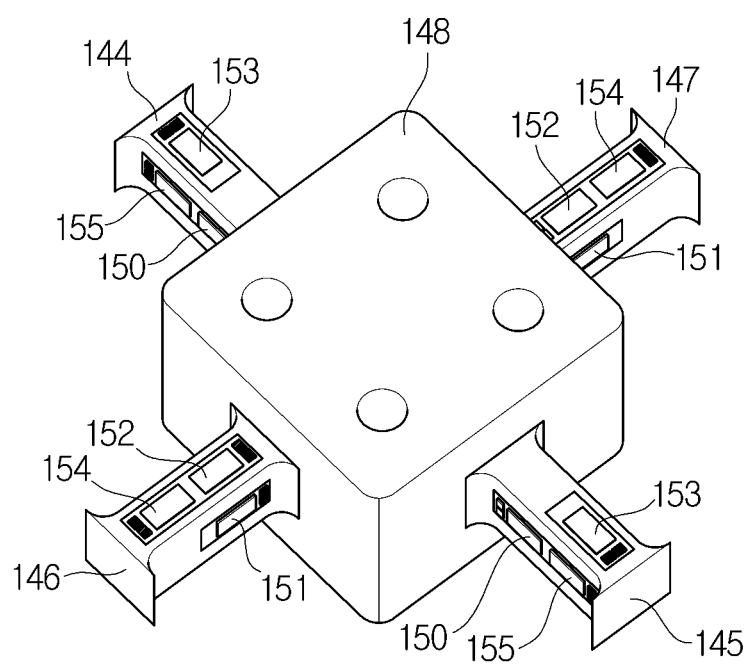
FIG. 10 is a perspective view illustrating the positions of the strain gauges mounted on the cross-shaped beam structure of FIG. 8 in accordance with one example.

FIG. 6 is a perspective view illustrating a force/torque sensor 126 of the radiographic system of FIGS. 1-3 in accordance with one example. FIG. 7 is an exploded perspective view illustrating the force/torque sensor 126 of FIG. 6 and brackets 127 and 128 for mounting the force/torque sensor 126 of FIG. 6 in accordance with one example. FIG. 8 is a perspective view illustrating a cross-shaped beam structure inside the force/torque sensor 126 of FIGS. 6 and 7 in accordance with one example. FIG. 9 is a front view illustrating the positions of strain gauges 150 to 155 mounted on the cross-shaped beam structure of FIG. 8 in accordance with one example. FIG. 10 is a perspective view illustrating the positions of the strain gauges 150 to 155 mounted on the cross-shaped beam structure of FIG. 8 in accordance with one example. FIG. 11 is a block diagram illustrating the force/torque sensor 126 of FIGS. 6-10 in accordance with one example.

Although the measurement unit 126 in this example is implemented with the force/torque sensor 126, the measurement unit 126 is not limited thereto, and the measurement unit 126 may be implemented with various types of sensors capable of measuring a force acting on the photographic unit 70, such as a three-axis force sensor.

The force/torque sensor 126 may measure forces in three directions intersecting with one another, and torques having the three directions as rotation axes.

Since the force/torque sensor 126 is able to measure a total of three forces in three directions and a total of three torques having the three directions as rotation axes, the force/torque sensor 126 is able to measure forces in the first direction D1 to the third direction D3 of movement of the photographic unit 70 and torques in the fourth direction D4 and the fifth direction D5 of the movement of the photographic unit 70.

Although the measurement unit 126 may be implemented with the force/torque sensor 126 to measure the forces in the three directions intersecting one another and the torques having the three directions as rotation axes, the measurement unit 126 is not limited thereto. Since the directions requiring a larger force of an operator in moving the photographic unit 70 are the three directions intersecting one another, the measurement unit 126 may be implemented with a three-axis sensor configured to measure forces acting in at least three directions to assist with the movement of the photographic unit 70.

Referring to FIG. 7, when the force/torque sensor 126 is mounted between the manipulating unit 80 and the photographic unit 70, a front surface member 140 of the force/torque sensor 126 is connected to a first bracket 127 configured to fix the force/torque sensor 126 to the manipulating unit 80, and a rear surface member 143 containing a cross-shaped beam structure 142 is connected to a second bracket 128 configured to fix the force/torque sensor 126 to the photographic unit 70. Although the first bracket 127 and the second bracket 128 are used to mount the force/torque sensor 126 between the manipulating unit 80 and the photographic unit 70 in this example, the method of mounting is not limited thereto, and the force/torque sensor 126 may be mounted between the manipulating unit 80 and the photographic unit 70 by use of a different mounting member or members. The front surface member 140 is separated from the rear surface member 143 by a connection member 141. The connection member 141 is not fastened to both the front surface member and the rear surface member, which enables the front surface member 140 to rotate relative to the rear surface member 143 when a torque is applied to the force/torque sensor 126. However, the connection member 141 may be omitted from the force/torque sensor 126.

The front surface member 140 has the form of the letter 'T' when viewed from the side, and is inserted into the rear surface member 143 through the connection member 141 to assemble the force/torque sensor 126. An insertion part 140a of the front surface member 140 corresponding to the stem of the letter 'T' is inserted into the rear surface member 143 through the connection member 141 and is fastened to a central portion 148 of the cross-shaped beam structure 142 mounted inside the rear surface member 143 to transmit the force or the torque applied to the manipulating unit 80 to the cross-shaped beam structure 142.

Since the insertion part 140a of the front surface member 140 is fastened to the central portion 148 of the cross-shaped beam structure 142, the central portion 148 of the cross-shaped beam structure 142 rotates with the front surface member 140 when a torque is applied to the force/torque sensor 126. Also, the outer rim of the cross-shaped beam structure 142 is fastened to the rear surface member 143 to prevent the outer rim of the cross-shaped beam structure 142 from rotating when a torque is applied to the force/torque sensor. This enables the central portion 148 of the cross-shaped beam structure 142 to rotate relative to the outer rim of the cross-shaped beam structure 142 when a torque is applied to the force/torque sensor 126.

A strain occurs in the cross-shaped beam structure 142 due to the force or torque transmitted through the front surface member 140, and this strain is measured by the strain gauges 150 to 155 mounted on the cross-shaped beam structure 142 as a change in resistance of the strain gauges 150 to 155. Although the cross-shaped beam structure 142 is used to measure the force or torque in this example, the force/torque sensor 126 is not limited to the cross-shaped beam structure 142, and a different structure may be used to measure the force or torque.

Referring to FIG. 8, the cross-shaped beam structure 142 is illustrated as being provided inside the rear surface member 143 of the force/torque sensor 126. The cross-shaped beam structure 142 will undergo a bending deformation corresponding to the force or torque applied from the outside. The strain gauges 150 to 155 are provided on surfaces of beams 144, 145, 146, and 147 as shown in FIGS. 9 and 10, and a resistance of each of the strain gauges 150 to 155 changes in proportion to the bending of the beam.

In order to measure the forces acting in the directions of the three axes intersecting one another, that is, the X axis, the Y-axis, and the Z-axis, four strain gauges 150 are provided the X-axis, four strain gauges 151 are provided for the Y-axis, and four strain gauges 152 are provided for the Z-axis.

For example, referring to FIGS. 9 and 10, in order to measure the force acting in the direction of the X-axis, four strain gauges 150 are provided on each lateral side of each of two beams 144 and 145 that are parallel to the Y-axis in the cross-shaped beam structure 142. In order to measure the force acting in the direction of the Y-axis, four strain gauges 151 are provided on each lateral side of each of two beams 146 and 147 that are parallel to the X-axis in the cross-shaped beam structure 142. In order to measure the force acting in the direction of the Z-axis, four strain gauges 152 are provided on a front and a rear of each of the two beams 146 and 147 that are parallel to the X-axis in the cross-shaped beam structure 142. In FIG. 9, the Z-axis is perpendicular to the plane of FIG. 9, and extends out of the plane of FIG. 9 as indicated by the dot in the circle at the intersection of the X-axis and the Y-axis.

In order to measure the torque having the X-axis as a rotation axis, four strain gauges 153 are provided on a front and a rear of each of the two beams 144 and 145 that are parallel to the Y-axis in the cross-shaped beam structure 142. In order to measure the torque having the Y-axis as a rotation axis, four strain gauges 154 are provided on a front and a rear of each of the two beams 146 and 147 that are parallel to the X-axis in the cross-shaped beam structure 142. In order to measure the torque having the Z-axis as a rotation axis, four strain gauges 155 are provided on each lateral side of each of the two beams 144 and 145 that are parallel to the Y-axis in the cross-shaped beam structure 142.

The installation positions and the number of the strain gauges 150 to 155 may be determined by the number of forces and torques to be measured, and are not limited to the positions and number described above.

The strain gauges 150 to 155 are connected in a bridge circuit. The bridge circuit may be implemented as a quarter bridge including a single strain gauge, a half bridge including two strain gauges, and a full bridge including four strain gauges. The bridge circuit in this example is implemented as a full bridge.

The full bridge is not easily affected by the temperature, and produces a small noise, and thus is suitable for a case where a high precision is required or a noise has a significant influence. In addition, the full bridge has a great ratio of output voltage to input voltage, and thus is suitable for the bridge circuit from the viewpoint of sensitivity.

In order to measure the forces acting in the three directions intersecting one another and the torques having the three directions as rotation axes as described above, a total of six sets of four strain gauges are provided, and a total of six full bridges are provided. That is, the four strain gauges 150 form a first set of four strain gauges and are connected in a first full bridge. The four strain gauges 151 form a second set of four strain gauges and are connected in a second full bridge. The four strain gauges 152 form a third set of four strain gauges and are connected in a third full bridge. The four strain gauges 153 form a fourth set of four strain gauges and are connected in a fourth full bridge. The four strain gauges 154 form a fifth set of four strain gauges and are connected in a fifth full bridge. The four strain gauges 155 form a sixth set of four strain gauges and are connected in a sixth full bridge.

The description of the force/torque sensor and the internal structure provided above is merely an example, and the measurement unit 126 is not limited thereto, and a different type of force/torque sensor having a different internal structure may be used.

The strain gauges used in the force/torque sensor 126 in this example may be a dual strain gauge having two strain gauges or a single strain gauge having only one strain gauge. In the following description, the reference number '150' will be used as a representative reference number of the strain gauge, but the description also applies to the strain gauges 151, 152, 153, 154, and 155.

A change in the resistance of the strain gauge 150 is converted to a voltage signal of microvolts or millivolts. As shown in FIG. 11, the voltage signal is amplified by an amplification unit 130 of the force/torque sensor 126. The amplified voltage signal is converted to a digital signal by an A/D converter (ADC) 132 included in a sensor control unit 131 of the force/torque sensor 126.

A firmware 133 of the sensor control unit 131 of the force/torque sensor 126 converts the digital signal to numerical data, and calculates effective data by performing a noise filtering operation and a calibration operation.

The firmware 133 converts the calculated data to adapt to a RS-232 communication protocol format that is defined between the system control unit 41 and the force/torque sensor 126 for transmission to the system control unit 41. The calculated data converted to adapt to the RS-232 communication protocol is converted to an electrical signal that conforms with the RS-232 standard by a Universal Synchronous/Asynchronous Receiver/Transmitter (USART) 134, and is transmitted to the system control unit 41.

Analog signals, such as the force or the torque applied to the force/torque sensor 126, are converted to digital signals by the force/torque sensor 126, and are transmitted to the system control unit 41.

As described above, information related to the direction and the magnitude of a force or a torque measured by the force/torque sensor 126 is transmitted to the system control unit 41, and is used by the system control unit 41 to generate a control signal to control the operation of the motor unit 110.

The force/torque sensor 126 is disposed at a position near the photographic unit 70 to recognize the intention of the operator by measuring the force or torque applied to the photographic unit 70 by the operator.

For example, the force/torque sensor 126 is disposed between the manipulating unit 80 and the photographic unit 70 as shown in FIG. 3. In the manual movement mode, the operator grips the grips 82 and applies a force or a torque to the grip 82, so the force/torque sensor 126 is disposed between the manipulating unit 80 and the photographic unit 70 as shown in FIG. 3.

As shown in FIG. 3, the force/torque sensor 126 is mounted between the manipulating unit 80 and the photographic unit 70 by the first bracket 127 disposed between the force/torque sensor 126 and the manipulating unit 80, and the second bracket 128 disposed between the force/torque sensor 126 and the photographic unit 70. In FIG. 12, the force/torque sensor 126 is illustrated as being mounted between the manipulating unit 80 and the photographic unit 70 by the first bracket 127 and the second bracket 128.

Since the force/torque sensor 126 is disposed between the manipulating unit 80 and the photographic unit 70, the force or torque applied to the grip 82 of the manipulating unit 80 by the operator may be precisely measured by the force torque sensor 126.

Alternatively, the force/torque sensor 126 may be mounted between the photographic unit 70 and the rotating joint unit 60, and may be connected to each of the photographic unit 70 and the rotating joint unit 60. If the force/torque sensor 126 is disposed in this manner, if the operator applies a force or torque to the photographic unit 70 without using the grip 82, the force or torque may still be precisely measured by the force/torque sensor 126.

Signals generated by the force/torque sensor 126, the collision sensor 74 mounted on the photographic unit 70, the collision sensors 87 mounted on the manipulating unit 80, and the manipulating unit 80 are transmitted to the system control unit 41 via a link board 73. That is, the link board 73 serves to relay the signals from the force/torque sensor 126, the collision sensors 74 and 87, and the manipulating unit 80 to the system control unit 41. Accordingly, the link board 73 is integrated with signal lines configured to deliver signals from the force/torque sensor 126, the collision sensors and 74 and 87, and the manipulating unit 80 to the link board 73. In addition, the link board 73 may include an A/D converter to convert analog signals to digital signals, so that in a case where analog signals are included in the signals transmitted to the link board 73 from the force/torque sensor 126, the collision sensors 74 and 87, and the manipulating unit 80, the A/D converter of the link board 73 converts the received analog signal to digital signals, thereby transmitting all signals in the form of a digital signal to the system control unit 41. As described above, the link board 73 serves to relay signals from the force/torque sensor 126, the collision sensors 74 and 87, and the manipulating unit 80 to the system control unit 41, and also serves to convert any analog signals to digital signals using the A/D converter included in the link board 73.

The link board 73 is installed inside the photographic unit 70 at the position shown in FIGS. 12 and 13.

The signals transmitted to the system control unit 41 via the link board 73 are transmitted through a RS-232 communication cable connected to the link board 73. The RS-232 communication cable extends through a corrugated tube 75 capable of expanding and contracting, and is connected to the system control unit 41.

Referring to FIGS. 12 and 13, since the corrugated tube 75 is connected to an opening 76 provided at an upper surface of the photographic unit 70, the link board 73 may be installed at a position adjacent to the opening 76 to which the corrugated tube 75 is connected so that the RS-232 communication cable easily extends through the corrugated tube 75.

The opening 76 to which the corrugated tube 75 is connected may be provided at a position that does not interfere with a region of the X-ray tube 71 configured to generate X-rays. Referring to FIGS. 12 and 13, the opening 76 is provided at a region of the upper surface of the photographic unit 70 that is adjacent to a rear surface of the photographic unit 70 opposite to a front surface of the photographic unit 70 on which the manipulating unit 80 is installed. The link board 73 is installed at a lower side of the opening 76.

The corrugated tube 75 may be installed at a different position as long as it does not interfere with the region of the X-ray tube 71 configured to generate X-rays, and the link board 73 may be installed at a position adjacent to the corrugated tube 75 installed at the different position.

Since digital signals generated from the measurement results of the force/torque sensor 126 are transmitted to the system control unit 41 via the link board 73, the system control unit 41 receives information related to the force or the torque applied to the photographic unit 70 measured by the force/torque sensor 126, and generates a control signal to drive the motor unit 110 based on the received information.

In order to assist with a translation movement of the photographic unit 70, the system control unit 41, based on a result of measurement of the force/torque sensor 126, determines a motor of the motors 111, 112, and 113 of the motor unit 110 that is configured to move the photographic unit 70 in a direction corresponding to a result of measurement of forces in three directions intersecting one another, and then generates a control signal to control the operation of the determined motor of the motor unit 110. In one example, the system control unit 41 is capable of generating control signals to control two or more of the motors 111, 112, and 113 simultaneously to move the photographic unit 70 (X-ray source unit) in two or more of the directions D1, D2, and D3 simultaneously if forces in two or more of the three directions intersecting one another (X-axis force, Y-axis force, and Z-axis force) are simultaneously sensed by the measurement unit 126 (sensor unit).

In order to generate the control signal to assist with a translation movement of the photographic unit 70, the system control unit 41 uses information on forces acting in three directions intersecting one another.

When the photographic unit 70 is not moving, the motor unit 110 is coupled to a moving roller in a stopped state. Accordingly, if the photographic unit 70 is manually moved to a desired position, a clutch is required to disengage the motor unit 110 from the moving roller. In addition, in order to stop moving the photographic unit 70, a brake is required. The need to install the clutch and the brake during the manufacturing process of the radiographic system complicates the manufacturing process.

However, in this example, the force applied to the photographic unit 70 is measured and the motor unit 110 is driven in response to the measured force to assist with the movement of the photographic unit 70 in a direction in which the force is applied, thereby eliminating the need for the clutch and the brake that would otherwise be required to manually move the photographic unit 70. Accordingly, three clutches and three brakes required for translations in the three directions D1, D2, and D3 may be omitted in this example.

In order to assist with a rotation movement of the photographic unit 70, the system control unit 41, based on a result of measurement of the force/torque sensor 126, determines a motor of the motors 114 and 115 of the motor unit 110 that is configured to rotate the photographic unit 70 in a direction corresponding to a result of measurement of a torque having one of the intersecting three directions as a rotation axis, and generates a control signal to control the operation of the determined motor of the motor unit 110.

In order to generate a control signal to assist with a rotation movement of the photographic unit 70, the system control unit 41 uses information on at least one torque having at least one of the three directions as a rotation axis. In this example, the directions in which the photographic unit 70 are the directions D4 and D5, and accordingly the force/torque sensor 126 measures torques acting in the directions D4 and D5.

When the photographic unit 70 is not rotating, the motor unit 110 is coupled to a moving roller in a stopped state. Accordingly, if the photographic unit 70 is manually rotated to a desired position, a clutch is required to disengage the motor unit 110 from the moving roller. In addition, in order to stop rotating the photographic unit 70, a brake is required. The need to install the clutch and the brake during the manufacturing process of the radiographic system complicates the manufacturing process.

However, in this example, the torque applied to the photographic unit 70 is measured and the motor unit 110 is driven in response to the measured torque to assist with the rotation of the photographic unit 70 in a direction in which the torque is applied, thereby eliminating the need for the clutch and brake that would otherwise be required to manually rotate the photographic unit 70. Accordingly, two clutches and two brakes required for rotation in the directions D4 and D5 may be omitted in this example.

As a result, in this example, the force or torque applied to the photographic unit 70 is measured, and the motor unit 110 is driven in response to the measured force or torque to assist with the movement or rotation of the photographic unit 70 in the direction in which the force or torque is applied, thereby eliminating the need for five clutches and five brakes that would otherwise be required to manually move or rotate the photographic unit 70.

Alternatively, if a smaller force is required to rotate the photographic unit 70 compared to a force required to translate the photographic unit 70, the radiographic system may assist with only the translation of the photographic unit 70 without assisting with the rotation of the photographic unit 70. In this case, two clutches and two brakes that may be omitted when the rotation of the photographic unit 70 is assisted need to be installed.

If the translation and the rotation of the photographic unit 70 are not assisted, in order to translate and rotate the photographic unit 70, a larger force is required. To this end, the manipulating unit 80 is provided at both sides of the photographic unit with two grips that are gripped by both hands.

However, in this example, when the translation and the rotation of the photographic unit 70 are assisted in the manual movement mode, the photographic unit 70 may be translated or rotated with a smaller force, so the grip 82 of the manipulating unit 80 is provided in a form that is gripped by one hand. Accordingly, the space required for the grip 82 is reduced in the manipulating unit 80, enabling the display unit 81 to be larger. The enlarged display unit 81 enables the operator to check more information at once without an additional manipulation of the manipulating unit 80, thereby reducing the time taken for manipulation of the radiographic system.

As described above, the operator may easily move the photographic unit 70 in a desired direction in the power-assisted mode. That is, when the operator moves the photographic unit 70 in a state in which the mode conversion unit 83 (which may also be referred to as a mode switching unit) is pressed by gripping the grip, the power-assisted mode is activated to assist with the movement of the photographic unit 70 regardless of the movement direction of the photographic unit 70. That is, the photographic unit 70 may be moved in any direction in the power-assisted mode.

However, in this example, a function of activating the power-assisted mode only when the photographic unit 70 is moved in a specific direction is provided. The button unit 84 of the manipulating unit 80 (which may also be referred to as an operating panel) is provided with first to third direction movement buttons 88, 89, and 90 for activating the power-assisted mode only when the photographic unit 70 is moved in any one of first to third directions. The first to third directions may be X, Y, and Z directions. For example, the first direction movement button 88 may activate the power-assisted mode only when the photographic unit 70 is moved in the X direction, the second direction movement button 89 may activate the power-assisted mode only when the photographic unit 70 is moved in the Y direction, and the third direction movement button 90 may activate the power-assisted mode only when the photographic unit 70 is moved in the Z direction.

When the operator applies a force for moving the photographic unit 70 in a corresponding direction while pressing a specific direction movement button, the measurement unit 126 measures the force applied to the photographic unit 70 and transmits information related to the measured force to the system control unit 41. The system control unit 41 assists with the movement of the photographic unit 70 by outputting a control signal for operating the motor that provides a driving force for moving the photographic unit 70 in the corresponding direction based on the information transmitted from the measurement unit 126 and driving the motor based on the control signal.

For example, when the operator moves the photographic unit 70 in the first direction while pressing the first direction movement button 88, the system control unit 41 activates the power-assisted mode only in the first direction and drives only the motor that provides a driving force for moving the photographic unit 70 in the first direction. When the photographic unit 70 is moved in another direction while the first direction movement button 88 is pressed, it is difficult to receive the assistance of the power-assisted mode in the movement of the photographic unit 70 because any motor for providing a driving force for moving the photographic unit 70 in a direction other than the first direction is not driven. The operator may release the activation of the power-assisted mode in the first direction by releasing the first direction movement button 88. The same is also true for manipulation of the second and third direction movement buttons 89 and 90.

As illustrated in FIG. 4, the operating panel 80 may be provided with the first, second, and third direction movement buttons 88, 89, and 90. The operator may activate the power-assisted mode only when moving the photographic unit 70 in a desired direction among the first to third directions. As illustrated in FIG. 4, the first, second, and third direction movement buttons 88, 89, and 90 may be implemented as hard key buttons, and additionally or alternatively may be implemented on the display unit 81 as soft key buttons. The first to third directions are only examples, and the specific direction movement buttons are not limited to these examples. For example, a specific direction movement button for activating the power-assisted mode only when the photographic unit 70 is moved in a specific direction that is a combination of any two or all three of the first to third directions may be provided.

Figure 5:
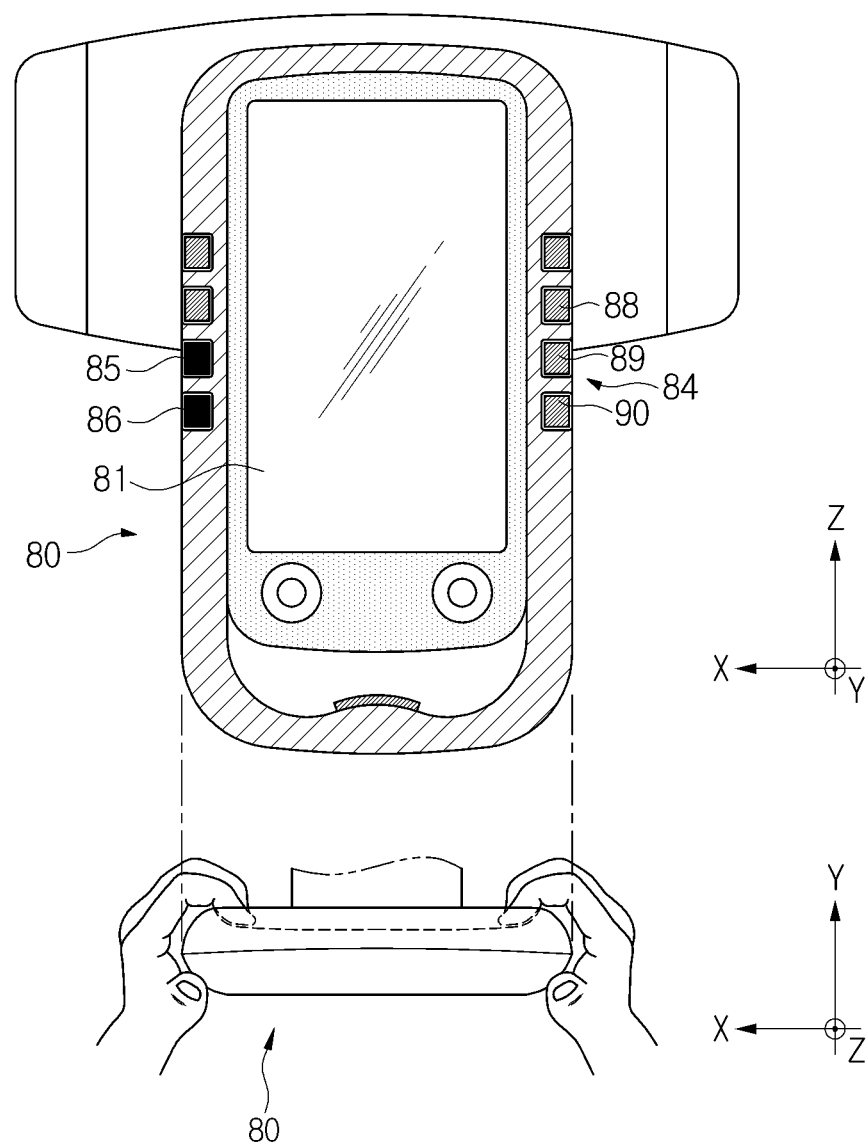
FIG. 5 is a diagram illustrating a state in which an operator grips the manipulating unit while pressing a specific direction movement button in accordance with one example.

FIG. 5 is a diagram illustrating a state in which the operator grips the operating panel 80 while pressing a specific direction movement button in accordance with one example. As illustrated in FIG. 5, a groove on which the operator's fingers may be stably placed is provided on a back side of the operating panel 80 so that the operator may more stably grip the operating panel 80. The operator may grip the operating panel 80 to move the photographic unit 70 as illustrated in FIG. 5 while pressing the specific direction movement button.

Although the above-described specific direction movement function may be configured to be performed in a state in which the specific direction movement button is pressed, the specific direction movement function is not limited thereto. For example, the specific direction movement function may be configured to be performed even when the pressed state is not maintained after the specific direction movement button has been pressed. In this case, by pressing the specific direction movement button again, the power-assisted mode for movement in the specific direction may be released.

Also, button unit 84 of the operating panel 80 may include a home position button that enables the operator to return the photographic unit 70 to a predetermined home position. The home position button may be implemented a hard key button as illustrated in FIG. 4, or implemented on the display unit 81 as a soft key button. When the operator presses a hard key home position button or touches a soft key home position button, the photographic unit 70 automatically moves to the predetermined home position. The home position may be pre-designated, stored, and changed as various home positions. When the home position button is manipulated, the system control unit 41 drives one or more motors needed to move the photographic unit 70 to the home position. When the photographic unit 70 reaches the home position, the system control unit 41 stops the movement of the photographic unit 70 at the home position by stopping the driving of the one or more motors.

Hereinafter, a process of generating a control signal to assist with a translation and a rotation of the photographic unit 70 based on the result of the measurement of the measurement unit 126 in the system control unit 41 will be described in detail with reference to FIG. 14.

Figure 14:
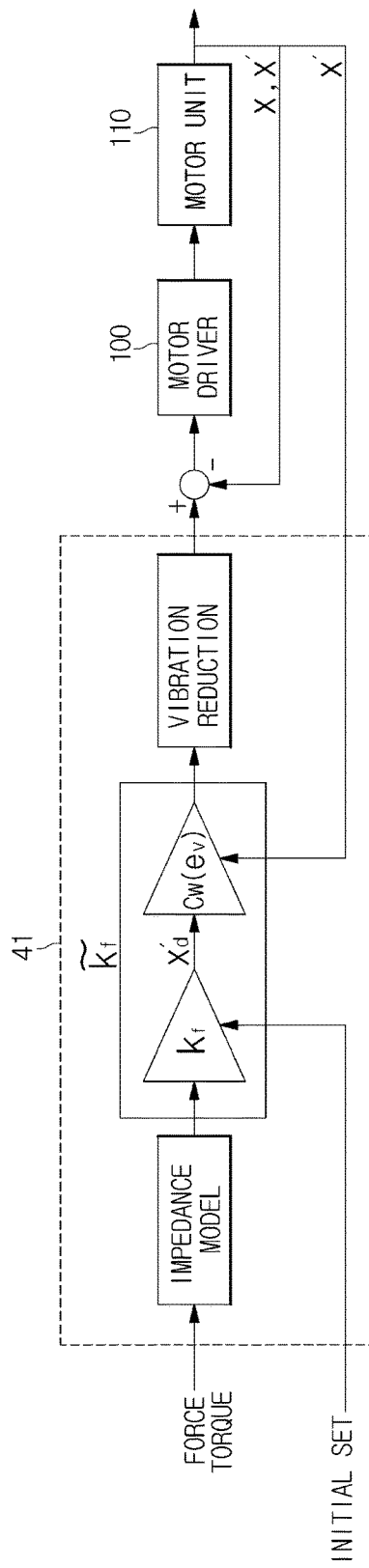
FIG. 14 is a control block diagram illustrating a process of generating a control signal to control a motor in a system control unit of the radiographic system of FIGS. 1-13 in accordance with one example.

FIG. 14 is a control block diagram illustrating a process of generating a control signal to control a motor in a system control unit of the radiographic system of FIGS. 1-13 in accordance with one example.

After the measurement unit 126 measures a force or a torque that are applied to the photographic unit 70, the system control unit 41 determines a motor of the motor unit 110 to provide a driving force in a direction of the force or the torque measured by the measurement unit 126.

For example, if the operator applies a force to the photographic unit 70 to move the photographic unit 70 in the first direction D1 while gripping the grip 82, the measurement unit 126 measures the force and transmits the measured force to the system control unit 41, and the system control unit 41 determines the first motors 111 that are configured to move the photographic unit 70 in the direction of the measured force transmitted from the measurement unit 126, that is, in the first direction D1, as a subject for control.

Similarly, if the operator applies a torque to the photographic unit 70 to rotate the photographic unit 70 in the fourth direction D4 while gripping the grip 82, the measurement unit 126 measures the torque and transmits the measured torque to the system control unit 41, and the system control unit 41 determines the fourth motor 114 that is configured to rotate the photographic unit 70 in a direction of the measured torque transmitted from the measurement unit 126, that is, in the fourth direction D4, as a subject of control.

Figure 15:
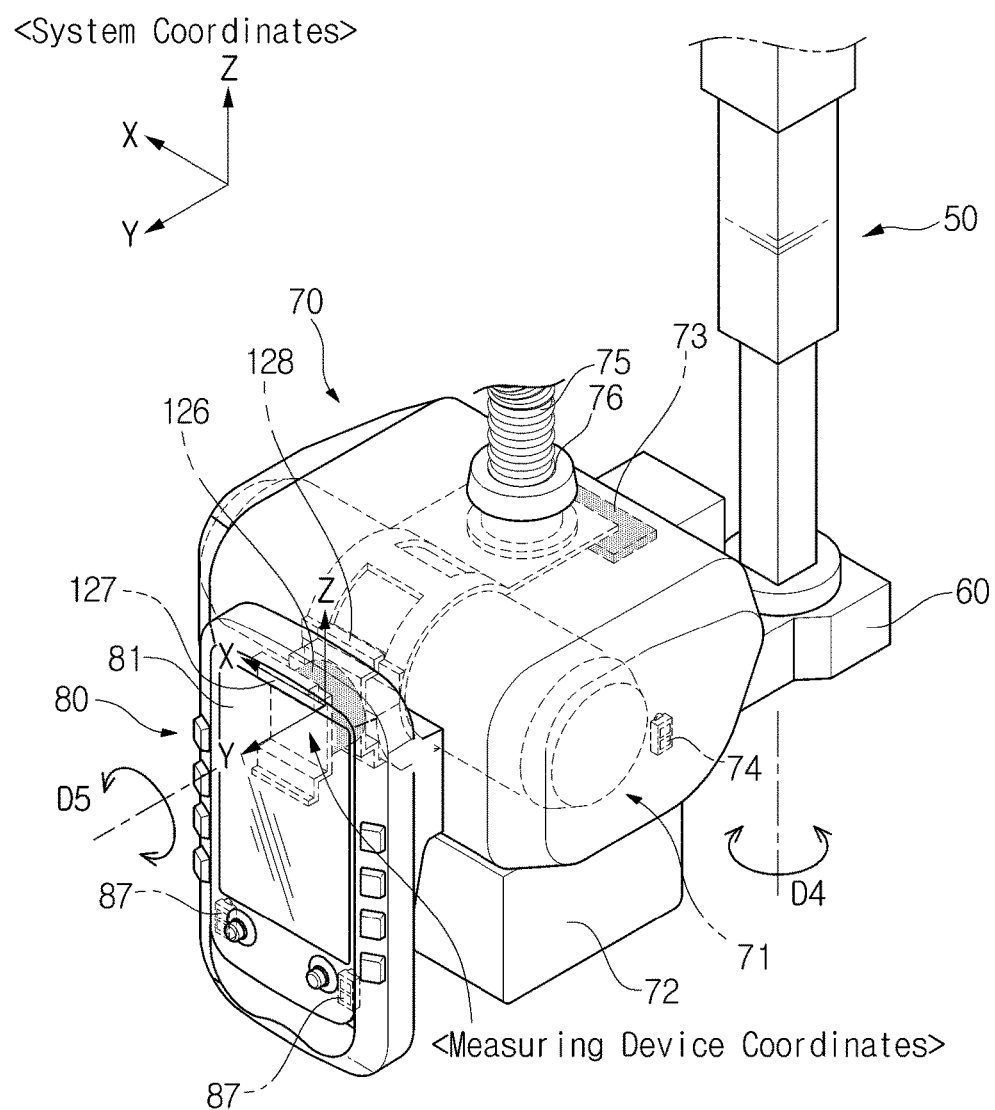
FIG. 15 is a diagram illustrating a state in which a coordinate system of a radiographic system is consistent with a coordinate system of the measuring unit in accordance with one example.

FIG. 15 is a diagram illustrating a state in which a coordinate system of the radiographic system is consistent with a coordinate system of the measuring unit 126 in accordance with one example. In FIG. 15, coordinate systems to be recognized by the operator in the movement of the photographic unit 70, that is, a coordinate system of the radiographic system and a coordinate system of the measurement unit 126, are illustrated. The measurement unit 126 measures a force or torque applied to the photographic unit 70 in the coordinate system of the measurement unit 126. At a position of the photographic unit 70 illustrated in FIG. 15, the coordinate system of the measurement unit 126 is consistent with the coordinate system of the radiographic system. That is, the X, Y, and Z axes of the coordinate system of the measurement unit 126 have the same orientation as the X, Y, and Z axes of the coordinate system of the radiographic system. Because the operator recognizes the coordinate system of the radiographic system and moves the photographic unit 70 according to the recognized coordinate system of the radiographic system, the coordinate system of the measurement unit 126 needs to be constantly consistent with the coordinate system of the radiographic system.

For example, as illustrated in FIG. 15, when the operator applies a force in an X-axis direction of the coordinate system of the radiographic system to move the photographic unit 70 in the first or X-axis direction in a state in which the coordinate system of the measurement unit 126 is consistent with the coordinate system of the radiographic system, a direction of the force applied to the photographic unit 70 detected by the measurement unit 126 (an X-axis direction of the coordinate system of the measurement unit 126) is consistent with the X-axis direction of the coordinate system of the radiographic system because the coordinate system of the measurement unit 126 is consistent with the coordinate system of the radiographic system. Accordingly, the system control unit 41 drives the motor that provides the driving force for moving the photographic unit 70 in the X-axis direction based on a detection result of the measurement unit 126.

Figure 16:
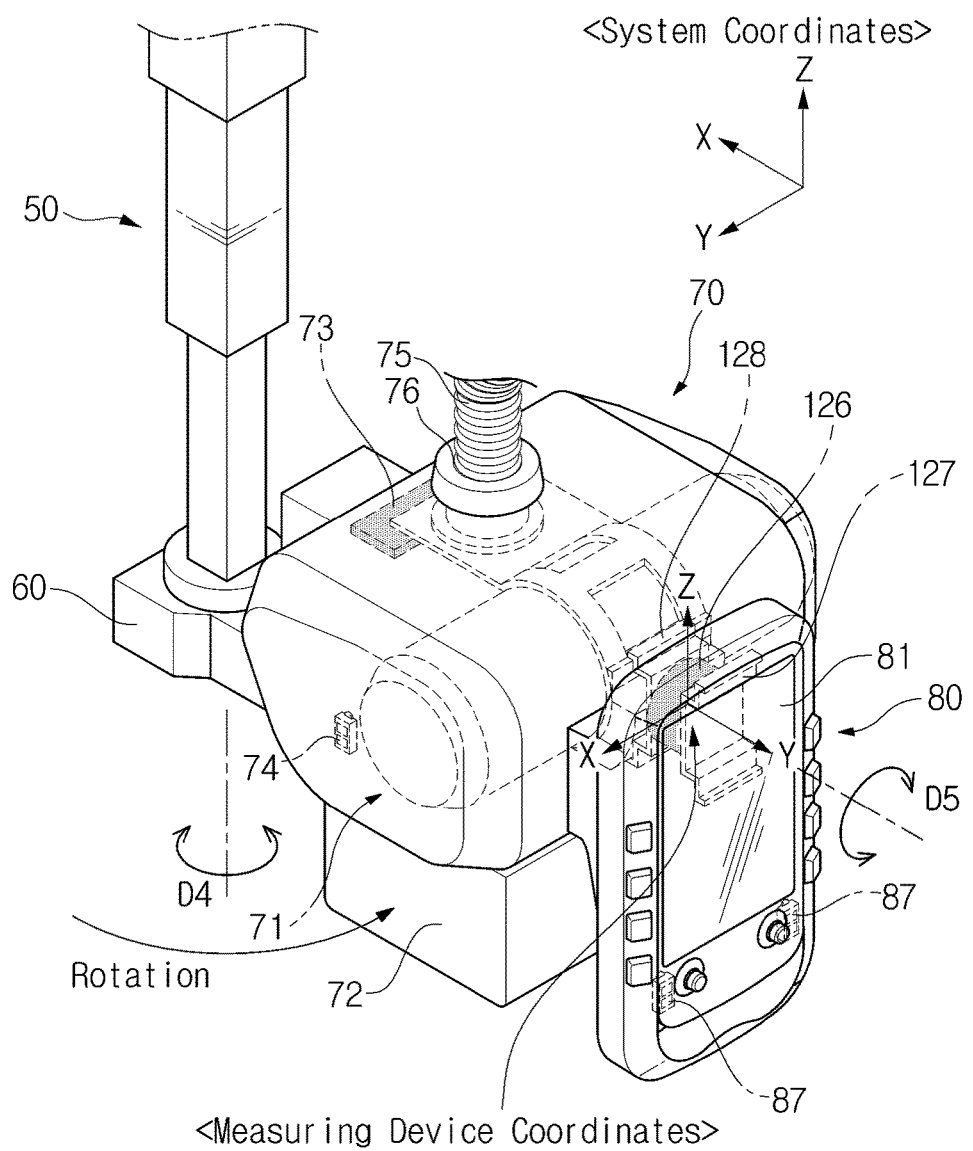
FIG. 16 is a diagram illustrating a state in which the coordinate system of the radiographic system is not consistent with the coordinate system of the measuring unit due to rotation of the photographic unit of the radiographic system in accordance with one example.

FIG. 16 is a diagram illustrating a state in which the coordinate system of the radiographic system is not consistent with the coordinate system of the measuring unit 126 due to rotation of the photographic unit 70 of the radiographic system in accordance with one example. As illustrated in FIG. 16, when the photographic unit 70 is rotated by 90 degrees in the fourth direction D4, the X-axis direction of the coordinate system of the measurement unit 126 becomes a Y-axis direction of the coordinate system of the radiographic system, and therefore the coordinate system of the measurement unit 126 is not consistent with the coordinate system of the radiographic system. That is, the X, Y, and Z axes of the coordinate system of the measurement unit 126 do not have the same orientation as the X, Y, and Z axes of the coordinate system of the radiographic system. In this state, when the operator applies a force in the X-axis direction of the coordinate system of the radiographic system to move the photographic unit 70 in the first or X-axis direction, the coordinate system of the measurement unit 126 is not consistent with the coordinate system of the radiographic system, and therefore a direction of a force applied to the photographic unit 70 detected by the measurement unit 126 becomes the Y-axis direction. Accordingly, if coordinate conversion for making the coordinate system of the measurement unit 126 to be consistent with the coordinate system of the radiographic system is not performed, the system control unit 41 will drive the motor providing the driving force for moving the photographic unit 70 in the second or Y-axis direction according to a detection result of the measurement unit 126 instead of driving the motor providing the driving force for moving the photographic unit 70 in the first or X-axis direction in which the operator desires to move the photographic unit 70. Also, when the photographic unit 70 is rotated by 90 degrees in the fifth direction D5 (not shown), the X-axis direction of the coordinate system of the measurement unit 126 becomes a Z-axis direction of the coordinate system of the radiographic system, and therefore the coordinate system of the measurement unit 126 is not consistent with the coordinate system of the radiographic system.

Accordingly, in this example, the coordinate system of the measurement unit 126 is made to be consistent with the coordinate system of the radiographic system by performing a coordinate conversion in real time to prevent the coordinate system of the measurement unit 126 from being inconsistent with the coordinate system of the radiographic system due to rotation of the photographic unit 70 in the fourth or fifth direction.

The system control unit 41 causes a direction of a force measured in the coordinate system of the measurement unit 126 to be consistent with the coordinate system of the radiographic system by performing a coordinate conversion defined by the following Equation 1.

$$\begin{Bmatrix} Fx_{ceiling} \\ Fy_{ceiling} \\ Fz_{ceiling} \end{Bmatrix} = \begin{bmatrix} \cos\beta & 0 & \sin\beta \\ 0 & 1 & 0 \\ -\sin\beta & 0 & \cos\beta \end{bmatrix} \cdot \begin{bmatrix} \cos\gamma & -\sin\gamma & 0 \\ \sin\gamma & \cos\gamma & 0 \\ 0 & 0 & 1 \end{bmatrix} \cdot \begin{Bmatrix} Fx_{sensor} \\ Fy_{sensor} \\ Fz_{sensor} \end{Bmatrix} \quad (1)$$

-continued $$= \begin{bmatrix} \cos\beta\cos\gamma & -\sin\gamma & \sin\beta\cos\gamma \\ \cos\beta\sin\gamma & \cos\gamma & \sin\beta\sin\gamma \\ -\sin\beta & 0 & \cos\beta \end{bmatrix} \cdot \begin{Bmatrix} Fx_{sensor} \\ Fy_{sensor} \\ Fz_{sensor} \end{Bmatrix}$$

Equation 1 represents an operation of converting a force ($Fx_{sensor}$, $Fy_{sensor}$, $Fz_{sensor}$) of X, Y, and Z directions measured in the coordinate system of the measurement unit 126 to a force ($Fx_{ceiling}$, $Fy_{ceiling}$, $Fz_{ceiling}$) in the coordinate system of the radiographic system through a coordinate conversion. In Equation 1, $\beta$ represents a rotation angle of the photographic unit 70 in the fifth direction D5, and $\gamma$ represents a rotation angle of the photographic unit 70 in the fourth direction D4.

A corresponding encoder or potentiometer may be provided to measure the rotation angle of the photographic unit 70 in each of the fourth direction D4 and the fifth direction D5 in real time. Each encoder or potentiometer may be included in a corresponding one of the fourth motor 114 and the fifth motor 115 for rotating the photographic unit 70 in a corresponding one of the fourth direction D4 and the fifth direction D5 as described above in connection with FIGS. 2 and 3. For example, when the photographic unit 70 rotates in the fourth direction D4, the corresponding encoder or potentiometer measures the rotation angle of the photographic unit 70 in the fourth direction D4 and outputs the measured rotation angle to the system control unit 41. The system control unit 41 converts a force measured in the coordinate system of the measurement unit 126 to a force in the coordinate system of the radiographic system using the measured rotation angle output from the encoder or the potentiometer and the coordinate conversion defined by Equation 1.

That is, when the operator applies a force in the X-axis direction of the coordinate system of the radiographic system to move the photographic unit 70 in the first or X-axis direction in a state in which the photographic unit 70 has been rotated in the fourth direction D4 and the measurement unit 126 detects a direction of the force applied to the photographic unit 70 in the coordinate system of the measurement unit 126, the system control unit 41 converts a force measured in the coordinate system of the measurement unit 126 to a force in the coordinate system of the radiographic system using the rotation angle measured by the encoder or the potentiometer and the coordinate conversion defined by Equation 1. When the force measured by the measurement unit 126 is converted to the force in the coordinate system of the radiographic system through the coordinate conversion, the system control unit 41 drives the motor that provides the driving force for moving the photographic unit 70 in the first or X-axis direction instead of driving the motor that provides the driving force for moving the photographic unit 70 in the second or Y-axis direction and assists the operator with moving the photographic unit 70 in the first or X-axis direction.

After the motor of the motor unit 110 capable of providing a driving force in the direction of the force or the torque measured by the measurement unit 126 is determined based on the force or the torque measured by the measurement unit 126, the system control unit 41 determines a driving speed of the determined motor of the motor unit 110 based on the magnitude of the force or the torque measured by the measurement unit 126.

Referring to FIG. 14, the system control unit 41 calculates a control signal including a driving speed of $x_d'$ of the determined motor of the motor unit 110 corresponding to the force or the torque applied to the photographic unit 70 based on an impedance model. A transfer function G(S) between a force F(S) applied to the photographic unit 70 and a driving speed V(S) of the photographic unit 70 is defined by the following Equation 2.

$$G(S) = \frac{V(S)}{F(S)} = k_f \frac{\omega_n^2}{S^2 + 2\zeta\omega_n S + \omega_n^2} \quad (2)$$

In Equation 2, $k_f$ denotes a speed/force ratio coefficient, and may be set by the operator depending on the requirements of the operator. In order to achieve a precise movement of the photographic unit 70, $k_f$ may be set to be smaller than a predetermined value, and in order to achieve an easy movement of the photographic unit 70, $k_f$ may be set to be larger than the predetermined value. $\zeta$ denotes a damping factor that is set to be larger than 1 to prevent an overshoot that may cause an unexpected movement of the photographic unit 70, and $\omega_n$ denotes an undamped natural frequency that is determined depending on the driving condition of the apparatus.

Although the transfer function G(S) is provided in the form of a second-order low-pass filter as shown in Equation 2, the transfer function G(S) is not limited thereto, and may be provided in the form of a first-order filter, or in the form of a third- or higher-order filter.

In addition, in a case in which a larger force is abruptly applied to the apparatus, for example, in a case in which an operator collides with the apparatus, or a larger force is applied to the apparatus due to an erroneous operation of the apparatus, the system control unit 41 prevents oscillation caused by such an abrupt larger force.

The system control unit 41 calculates a weighted speed/force ratio coefficient $\tilde{k}_f$ having a weight function applied thereto in real time in order to prevent oscillation. The following Equation 3 defines the weighted speed/force ratio coefficient $\tilde{k}_f$.

$$\tilde{k}_f = C_w(e_v)k_f, \; C_w(e_v) = 0.5\frac{e^{-a(|e_v|-b)} - 1}{e^{-a(|e_v|-b)} + 1} + 1 \quad (3)$$

In Equation 3, $C_w$ denotes a weight function, and $e_v$ denotes a speed error, that is, a difference between a driving speed $x_d'$ of the photographic unit 70 calculated through the impedance model and a speed $x'$ at which the photographic unit 70 actually moves, $k_f$ denotes the speed/force ratio coefficient set by the operator, and a and b denote adjustment constants.

An abrupt increase or decrease of a force being applied to the photographic unit 70 results in a speed error, that is, results in $e_v$ increasing, and with the increase of $e_v$, the weight function $C_w(e_v)$ decreases, and thus the weighted speed/force ratio coefficient $\tilde{k}_f$ decreases. Accordingly, the system has a high damping coefficient, and as the moving speed of the photographic unit 70 decreases or the photographic unit 70 stops moving, oscillation does not occur.

The degree to which the weight function $C_w(e_v)$ decreases as $e_v$ increases varies depending on the adjustment constant a. If the adjustment constant a is larger, the weight function $C_w(e_v)$ decreases nonlinearly. The weight function $C_w(e_v)$ starts decreasing in a nonlinear manner if the speed error $e_v$ exceeds a predetermined value, and thus the moving speed $x'$ of the photographic unit 70 decreases or the photographic unit 70 stops moving. A value of the speed error $e_v$ causing the weight function $C_w(e_v)$ to start decreasing may be set in advance depending on the value a and may be stored. Accordingly, if the speed error $e_v$ equals or exceeds the value of the speed error $e_v$ set in advance and stored, the system control unit 41 reduces the moving speed of the photographic unit 70 or stops moving the photographic unit 70.

After the system control unit 41 calculates the control signal including the driving speed $x_d'$ of the determined motor of the motor unit 110, the system control unit 41 removes a signal having a frequency range corresponding to a resonance frequency range of the radiographic system from the control signal to reduce vibration generated when the photographic unit 70 moves.

Figure 17:
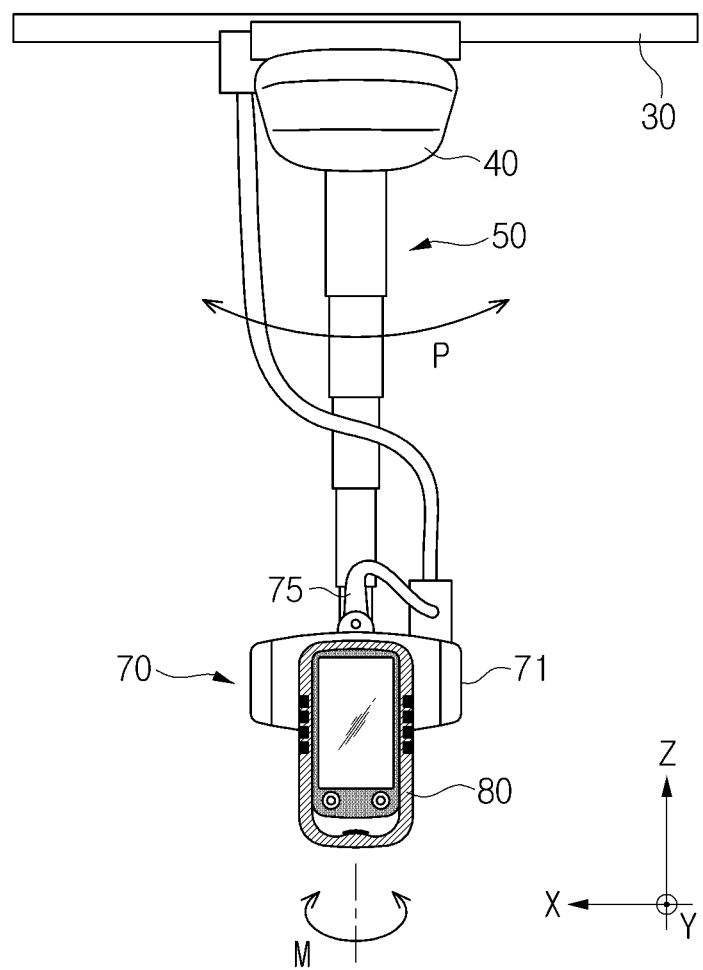
FIG. 17 is a diagram illustrating vibration of the radiographic system in accordance with one example.

FIG. 17 is a diagram illustrating vibration of the radiographic system in accordance with one example. Because the radiographic system has a structure in which the photographic unit 70 is mounted on a ceiling through the post frame 50, the combination of the post frame 50 and the photographic unit 70 may vibrate like a simple pendulum, that is, like a weight hung from a string, as illustrated by P in FIG. 17. For example, when a force is applied to move the photographic unit 70 in the X-axis direction, the force may cause the post frame 50 and the photographic unit 70 to vibrate like a simple pendulum as illustrated by P in FIG. 17, and the vibration may be amplified by resonance when the frequency of the vibration is equal to a natural frequency of the radiographic system.

Also, the photographic unit 70 of the radiographic system is connected to the rotating joint 61 and mounted outside an extension line of the post frame 50 without being mounted on the extension line of the post frame 50 as illustrated in FIGS. 2 and 3. Accordingly, the center of mass of the photographic unit 70 is not aligned with the center of the post frame 50. Because the center of mass of the photographic unit 70 is not aligned with the center of the post frame 50, the photographic unit 70 may rotationally vibrate about the post frame 50 as a rotation axis as illustrated by M in FIG. 17. For example, when a force is applied to move the photographic unit 70 in the X-axis direction, the force may cause the photographic unit 70 to rotationally vibrate as illustrated in FIG. 17, and the rotational vibration may be amplified by resonance when the frequency of the angular vibration is equal to a natural frequency of the radiographic system.

When a vibration is amplified by resonance, it may be difficult to accurately position the photographic unit 70 at a desired position, structural fatigue may accumulate in the parts of the radiographic system, or a fault may occur.

In this example, the amplification of the vibration by resonance is prevented from occurring by eliminating a signal of a frequency domain corresponding to a resonance frequency domain of the radiographic system from a control signal using a notch filter represented by Equation 4 below.

In addition, in this example, a lookup table LUT in which the natural frequency of the radiographic system, which may change according to the position of the photographic unit 70, is mapped to a space in which the photographic unit 70 is movable may be prestored. The system control unit 41 determines the natural frequency of the radiographic system corresponding to a movement position of the photographic unit 70 using the lookup table LUT every time the photographic unit 70 moves, and removes the signal of the frequency domain corresponding to the resonance frequency domain of the radiographic system from the control signal by applying the notch filter.

Figure 18:
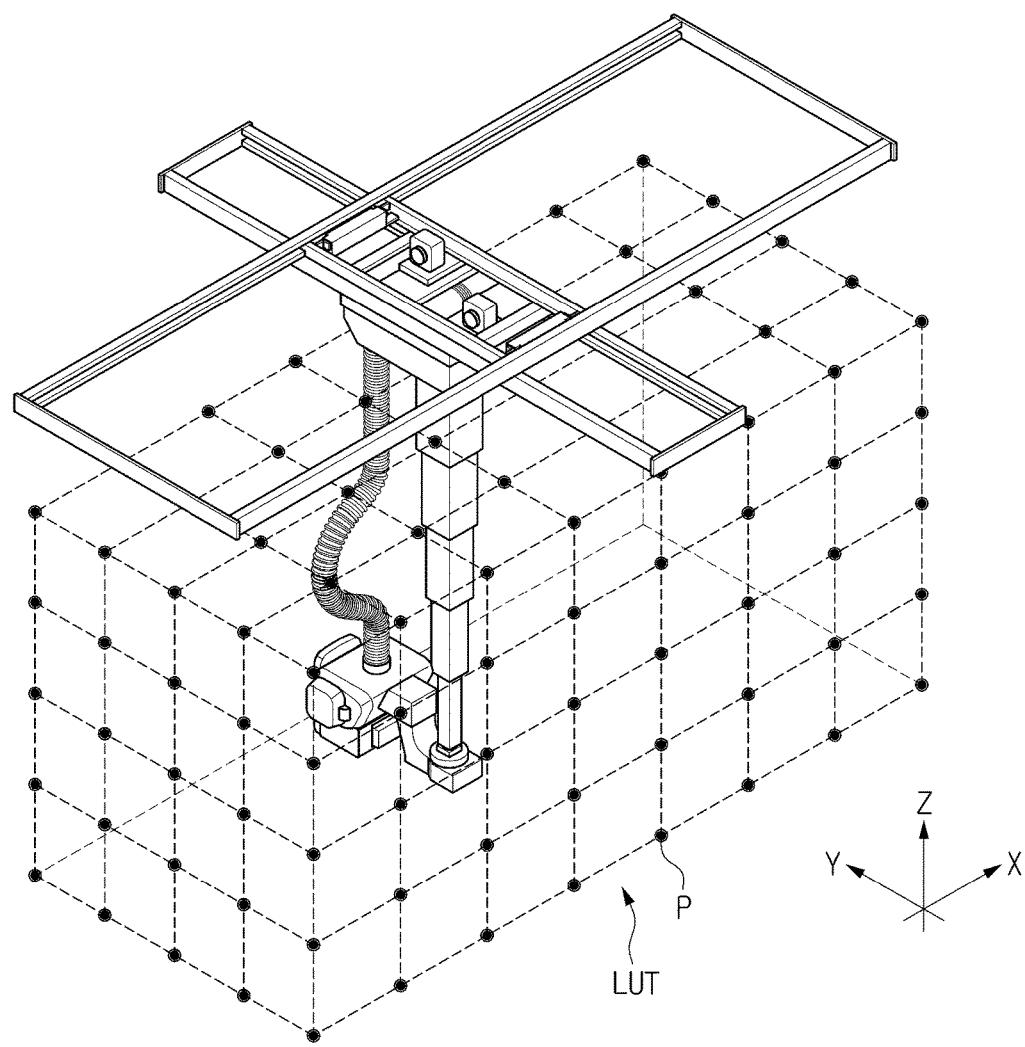
FIG. 18 is a diagram conceptually illustrating mapping to a three-dimensional virtual space representing a movement range of the radiographic system in a resonance frequency lookup table of the radiographic system in accordance with one example.

FIG. 18 is a diagram conceptually illustrating mapping to a three-dimensional virtual space representing a movement range of the radiographic system in a resonance frequency lookup table of the radiographic system in accordance with one example. In FIG. 18, the lookup table LUT in which the natural frequency of the radiographic system is mapped to predetermined points P of a three-dimensional virtual space corresponding to a space in which the photographic unit 70 is movable is conceptually illustrated. The predetermined points may be equally spaced in each of the X, Y, and Z directions as illustrated in FIG. 18, but this is merely an example, and the predetermined points are not limited to any particular spacing or configuration. The natural frequency of the radiographic system may have a different value at each predetermined point of the three-dimensional virtual space. For example, because the frequency of the simple pendulum vibration increases as the length of the post frame 50 decreases, a value of the natural frequency of the radiographic system may increase the photographic unit 70 moves closer to the ceiling.

The lookup table LUT may be stored in the system control unit 41. The system control unit 41 calculates the natural frequency of the radiographic system corresponding to a movement position of the photographic unit 70 detected in real time using the lookup table LUT.

That is, when the photographic unit 70 moves, the encoder or the potentiometer of the motor moving the photographic unit 70 detects the position of the photographic unit 70 and transmits a position change of the photographic unit 70 to the system control unit 41 in real time. The system control unit 41 determines natural frequency values mapped to predetermined points that are closest to the position of the photographic unit 70 detected in real time using the lookup table LUT, and calculates the natural frequency of the radiographic system corresponding to the position of the photographic unit 70 by interpolating the determined natural frequency values. The system control unit 41 removes a signal of the resonance frequency domain of the radiographic system by applying the calculated natural frequency to the notch filter.

A transfer function N(S) of a notch filter to remove a signal of a resonance frequency range is defined by the following Equation 4.

$$N(S) = \frac{S^2 + \omega_o^2}{S^2 + \frac{\omega_o}{Q}S + \omega_o^2} \quad (4)$$

In Equation 4, $\omega_o$ denotes a notch frequency that is a resonance frequency of the radiographic system, and Q denotes a quality factor. A stop bandwidth that is removed by the notch filter is determined by a ratio of the notch frequency to the quality factor, that is, $\omega_o/Q$.

In FIG. 14, the blocks labeled "IMPEDANCE MODEL" and "$k_f$" together perform a calculation according to Equation 2 above; the block labeled "$C_w(e_v)$" performs a calculation according to Equation 3 above, and the block labeled "VIBRATION REDUCTION" performs a calculation according to Equation 4 above. The input labeled "INITIAL SET" enables the operator to set $k_f$ to a desired value.

One control circuit as shown in FIG. 14 is provided for each of the motors 111, 112, 113, 114, and 115 of the motor unit 110. However, only one control circuit may be provided for the two motors 111. The control circuit provided for the two motors 111 receives a force measured in the direction D1 by the measurement unit 126 as an input. The control circuit provided for the motor 112 receives a force measured in the direction D2 by the measurement unit 126 as an input. The control circuit provided for the motor 113 receives a force measured in the direction D3 by the measurement unit 126 as an input. The control circuit provided for the motor 114 receives a torque measured in the direction D4 as an input. The control circuit provided for the motor 115 received a torque measured in the direction D5 as an input. In an example in which the radiographic system assists only with the translation of the photographic unit 70 without assisting with the rotation of the photographic unit 70 as described above, one control circuit as shown in FIG. 14 is provided for each of the motors 111, 112, and 113 of the motor unit 110. Again, only one control circuit may be provided for the two motors 111.

The system control unit 41 applies the notch filter to the calculated control signal, and converts the calculated control signal to which the notch filter has been applied to a form satisfying the CANopen (Controller Area Network open) communication profile DS-402, and transmits the converted control signal to the motor driver 100.

The communication between the system control unit 41 and the motor driver 100 in this example supports the CANopen communication profile DS-301, DS-305, DS-402 industrial standard profile based on a CAN communication interface. The communication between the system control unit 41 and the motor driver 100 may be achieved through a CAN communication cable.

The motor driver 100 generates a three-phase AC voltage signal to drive the determined motor of the motor unit 110 according to the control signal transmitted from the system control unit 41, and outputs the generated three-phase AC voltage signal to the determined motor of the motor unit 110. The determined motor of the motor unit 110, according to the voltage signal transmitted from the motor driver 100, assists the photographic unit 70 in the movement in the direction of the force or the torque measured by the measurement unit 126. Referring to FIG. 14, the motor unit 110 feeds back the driving speed x' and the moving distance x of the determined motor to the system control unit 41. The system control unit 41 updates the control signal in real time based on the feedback information, thereby performing a precise assistance.

Accordingly, when the photographic unit 70 is moved to a desired position with the assistance of the motor unit 110, the operator may move the photographic unit 70 with a smaller force or torque, thereby reducing the fatigue caused by the manual manipulation of the photographic unit 70.

When the operator desires to stop the movement of the photographic unit 70 at a target position while moving the photographic unit 70 in the power-assisted mode, it is difficult to accurately stop the movement of the photographic unit 70 at the target position in one attempt. In general, the photographic unit 70 is located at the target position while the moving speed of the photographic unit 70 is reduced and the position of the photographic unit 70 is finely controlled to stop the photographic unit 70 at the target position.

A radiographic system in accordance with one example may automatically stop the photographic unit 70 at the target position without the need to finely control the position of the photographic unit 70 in the vicinity of the target position to accurately stop the photographic unit 70 at the target position.

That is, when the moving speed of the photographic unit 70 is less than or equal to a preset speed at a preset specific position, the system control unit 41 stops the photographic unit 70 at the preset specific position by stopping the driving of the motor that is assisting with the movement of the photographic unit 70. That is, the movement of the photographic unit 70 is stopped by stopping the driving of the motor without using a separate brake. Hereinafter, a mode in which this function is implemented and is referred to as a virtual detent mode as will be described.

In the virtual detent mode, the operator may directly designate and store a position at which the movement of the photographic unit 70 is to be automatically stopped, and this position may be preset and stored as a position at which the photographic unit 70 is frequently located. For example, the position at which the photographic unit 70 is located may be a home position at which the photographic unit 70 is located while the radiographic system is not being used. Hereinafter, this preset position is referred to as a stop position. The encoder or the potentiometer described above detects the position of the photographic unit 70 in real time and transmits the detected position to the system control unit 41. The system control unit 41 determines whether the position of the photographic unit 70 detected in real time is equal to the stop position.

In addition, a speed sensor for detecting the moving speed of the photographic unit 70 detects the moving speed of the photographic unit 70 in real time and transmits the detected moving speed to the system control unit 41. The speed sensor may be the encoder or the potentiometer described above, or may be a separate speed sensor. The system control unit 41 determines whether the moving speed of the photographic unit 70 detected in real time is less than or equal to the preset speed at the stop position. Hereinafter, the preset speed is referred to as a first reference speed. Because it may be assumed that the operator desires to stop the movement of the photographic unit 70 at the stop position when the speed of the photographic unit 70 is sufficiently slow at or near the stop position, the first reference speed may be determined from this viewpoint.

When the position of the photographic unit 70 is equal to the stop position and the moving speed of the photographic unit 70 is less than or equal to the first reference speed, the system control unit 41 is configured to stop the movement of the photographic unit 70 by stopping the driving of the motor that is assisting with the movement of the photographic unit 70.

In accordance with another example, the system control unit 41 may determine whether the real-time position of the photographic unit 70 transmitted from the encoder or the potentiometer has entered a space (hereinafter referred to as a stop space) having a predetermined volume including the stop position. In addition, when the position of the photographic unit 70 has entered the stop space, the system control unit 41 determines whether the moving speed of the photographic unit 70 transmitted in real time is less than or equal to the first reference speed, and gradually reduces the moving speed of the photographic unit 70 so that the photographic unit 70 may stop at the stop position when the moving speed of the photographic unit 70 is less than or equal to the first reference speed. Because it is possible to stop the photographic unit 70 while gradually reducing the moving speed of the photographic unit 70 without immediately stopping the photographic unit 70 by setting the stop space, the photographic unit 70 may more smoothly stop at the stop position.

An input unit such as a button capable of turning on and off the above-described virtual detent mode if necessary may be provided on the operating panel 80 or the workstation.

The operator may move the photographic unit 70 to the preset stop position by turning on the virtual detent mode by manipulating the button and controlling the moving speed of the photographic unit 70 to be less than or equal to the first reference speed at the stop position so that the photographic unit 70 will stop at the stop position. Alternatively, after turning on the virtual detent mode, the operator may control the moving speed of the photographic unit 70 to be less than or equal to the first reference speed when the photographic unit 70 enters the stop space so that the system control unit 41 will gradually reduce the moving speed of the photographic unit 70 to stop the photographic unit 70 at the stop position.

In accordance with another example, when the photographic unit 70 is close to an end of the first guide rail 31 or the second guide rail 32 in FIGS. 2 and 3, the system control unit 41 causes the movement of the photographic unit 70 to stop by stopping the motor in operation regardless of whether the virtual detent mode is turned on or off and regardless of the moving speed of the photographic unit 70 to prevent the photographic unit 70 from running off the end of the first guide rail 31 or the second guide rail 32.

The virtual detent mode has an advantage in that noise or vibration of the radiographic system due to using a brake to stop the photographic unit 70 may be prevented because the movement of the photographic unit 70 is stopped by stopping the driving of the motor without using the brake. Furthermore, the brake itself may be omitted as described above.

When the operator desires to stop the movement of the photographic unit 70 at a target position while moving the photographic unit 70 in the power-assisted mode, it is difficult to accurately stop the position of the photographic unit 70 at the target position in one attempt. When the above-described virtual detent mode is not used, the photographic unit 70 is generally located at the target position while the moving speed of the photographic unit 70 is reduced and the position of the photographic unit 70 is finely controlled.

In the power-assisted mode, a movement sensitivity of the photographic unit 70, that is, a ratio (velocity/force) of the moving speed of the photographic unit 70 to a force applied to move the photographic unit 70, may be set to be large so that the operator may move the photographic unit 70 with a small force. As the movement sensitivity increases, the magnitude of the force necessary to move the photographic unit 70 decreases at a constant moving speed. Because the movement sensitivity is basically set to easily move the photographic unit 70 with the small force in the power-assisted mode, the photographic unit 70 may move farther than an intended distance even when the operator applies a small force to finely control the position of the photographic unit 70. Accordingly, a problem that it is difficult to finely control the position of the photographic unit 70 may occur.

Figure 19:
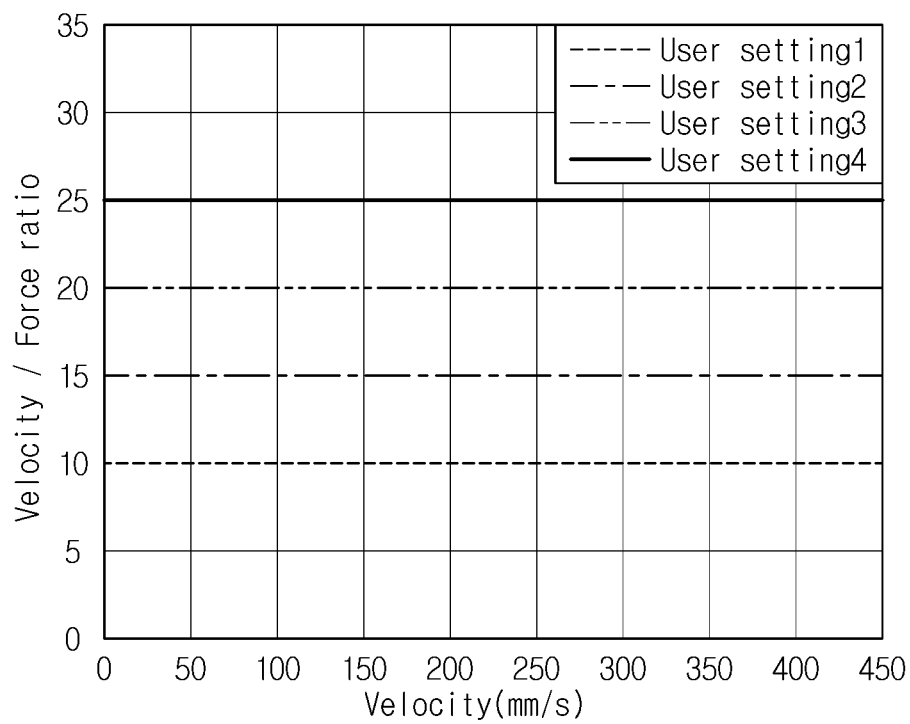
FIG. 19 is a graph illustrating a fixed movement sensitivity of the radiographic system in accordance with one example.

FIG. 19 is a graph illustrating a fixed movement sensitivity of the radiographic system in accordance with one example. As the movement sensitivity increases, the operator feels as if the photographic unit 70 is light when moving the photographic unit 70. In contrast, as the movement sensitivity decreases, the operator feels as if the photographic unit 70 is heavy. When it is necessary to finely control the position of the photographic unit 70, it is advantageous that the movement sensitivity be small so that the operator will feel as if the photographic unit 70 is heavy. This is because a difference between a movement distance of the photographic unit 70 intended by the operator and an actual movement distance of the photographic unit 70 should to be small when it is necessary to finely control the position of the photographic unit 70. However, when the photographic unit 70 is to be moved by a predetermined distance or more, it is advantageous that the movement sensitivity be large so that the operator will feel as if the photographic unit 70 is light. This is because it is advantageous for the magnitude of the force necessary to move the photographic unit 70 to be small. FIG. 19 illustrates four different fixed movement sensitivities corresponding to four user settings that may be selected by the operator using an input unit provided on the operating panel 80 or the workstation according to the operator's preference.

Because a force that needs to be applied to obtain a constant moving speed is small if a movement sensitivity value increases when the movement sensitivity is set to have a constant value as illustrated in FIG. 19, this is an advantage when the photographic unit 70 is to be moved by a predetermined distance or more. However, this is a disadvantage when the position of the photographic unit 70 is to be finely controlled because the photographic unit 70 may move farther than an intended distance. In contrast, if the movement sensitivity value decreases, this is an advantage when the position of the photographic unit 70 is to be finely controlled, but is a disadvantage when the photographic unit 70 is to be moved by a predetermined distance or more.

Accordingly, settings suitable for both when the photographic unit 70 is to be moved by a predetermined distance or more and when the position of the photographic unit 70 is to be finely controlled may be provided by setting a variable movement sensitivity.

Figure 20:
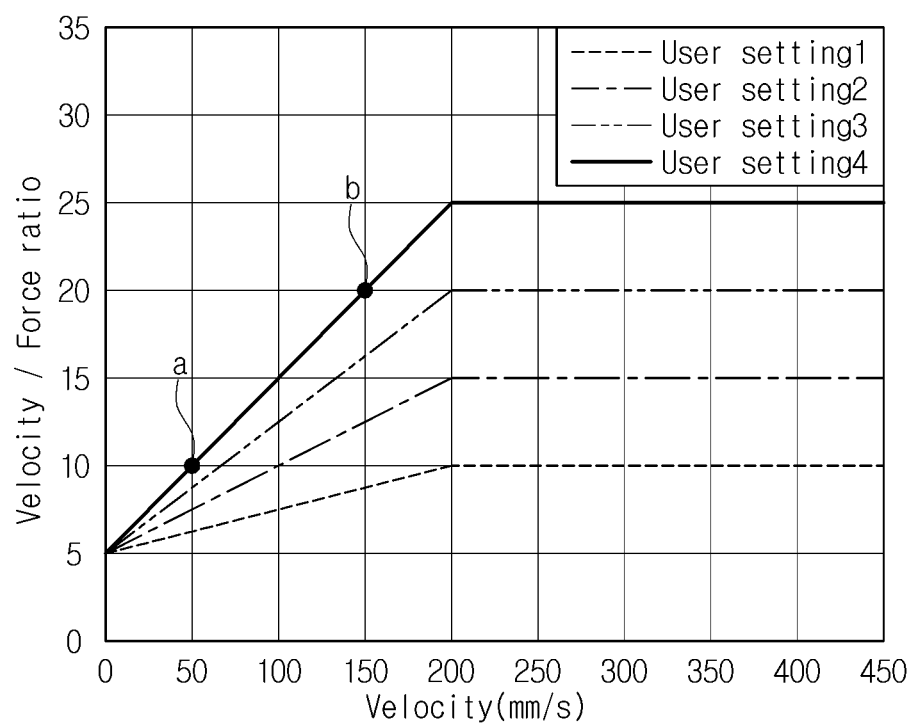
FIG. 20 is a graph illustrating a variable movement sensitivity of the radiographic system in accordance with one example.

FIG. 20 is a graph illustrating a variable movement sensitivity of the radiographic system in accordance with one example. As illustrated in FIG. 20, the movement sensitivity of the photographic unit 70 is fixed to a constant value when the moving speed of the photographic unit 70 is greater than a preset second reference speed (200 millimeters/second (mm/s)) in the example in FIG. 19), thereby providing a setting advantageous for the movement of the photographic unit 70. When the moving speed of the photographic unit 70 is less than or equal to the preset second reference speed, the movement sensitivity of the photographic unit 70 is set to be reduced as the moving speed of the photographic unit 70 is reduced, thereby providing a setting advantageous for the fine control of the photographic unit 70. FIG. 20 illustrates four different variable movement sensitivities corresponding to four user settings that may be selected by the operator using an input unit provided on the operating panel 80 or the workstation according to the operator's preference.

When the moving speed of the photographic unit 70 is less than or equal to the second reference speed, the movement sensitivity of the photographic unit 70 is reduced as the moving speed of the photographic unit 70 is reduced, and the operator may finely control the movement of the photographic unit 70 according to the operator's intention. For example, because a movement sensitivity (a) in FIG. 20 when the photographic unit 70 is being moved at a slow speed during fine control is less than a movement sensitivity (b) in FIG. 20 when the photographic unit 70 is being moved at a slightly faster speed during fine control, the operator may control the position of the photographic unit 70 with a higher precision than when the movement sensitivity value is fixed as in FIG. 19 even when the movement sensitivity value of the photographic unit 70 is small.

Because it may be assumed that the operator desires to finely control the position of the photographic unit 70 when the speed of the photographic unit 70 is sufficiently slow, the second reference speed may be determined from this viewpoint.

The variable movement sensitivity as illustrated in FIG. 20 may be preset and stored in the system control unit 41. The operator may set the movement sensitivity by selecting one of the fixed movement sensitivities illustrated in FIG. 19 or one of the variable movement sensitivities illustrated in FIG. 20.

An input unit such as a button capable of turning on and off the setting of the above-described variable sensitivity may be provided on the operating panel 80 or the workstation if necessary. The operator may set the variable movement sensitivity by manipulating the button if necessary.

When the variable movement sensitivity has been set, the speed sensor detects the moving speed of the photographic unit 70 in real time and transmits the detected moving speed to the system control unit 41. If the moving speed of the photographic unit 70 detected in real time is less than or equal to the second reference speed, the movement sensitivity is controlled according to a change in the speed of the photographic unit 70 as illustrated in FIG. 20.

As the photographic unit 70 is moved with the assistance of the motor unit 110, the system control unit 41 outputs an alarm sound indicating the movement of the photographic unit 70 from the sound output unit 42 shown in FIG. 1, thereby notifying the operator that the movement of the photographic unit 70 is achieved with the assistance of the motor unit 110.

Different types of alarm sounds corresponding to different movement modes of the photographic unit 70 may be stored in advance. For example, the alarm sounds may include an alarm sound indicating that the photographic unit 70 is being moved in the automatic movement mode, and an alarm sound indicating that the photographic unit 70 is being moved in the manual movement mode. Accordingly, the operator may recognize the current movement mode based on the type of alarm sound being output.

Other sounds to be output from the sound output unit 52 that are related to various motions of the radiographic system as well as the movement of the photographic unit 70 may be stored in advance. For example, various types of a camera shutter sound may be stored in advance so that a camera shutter sound is output when radiography is performed by the radiographic system. When radiography is performed, the camera shutter sound stored in advance may be output from the sound output unit 42.

Figure 21:
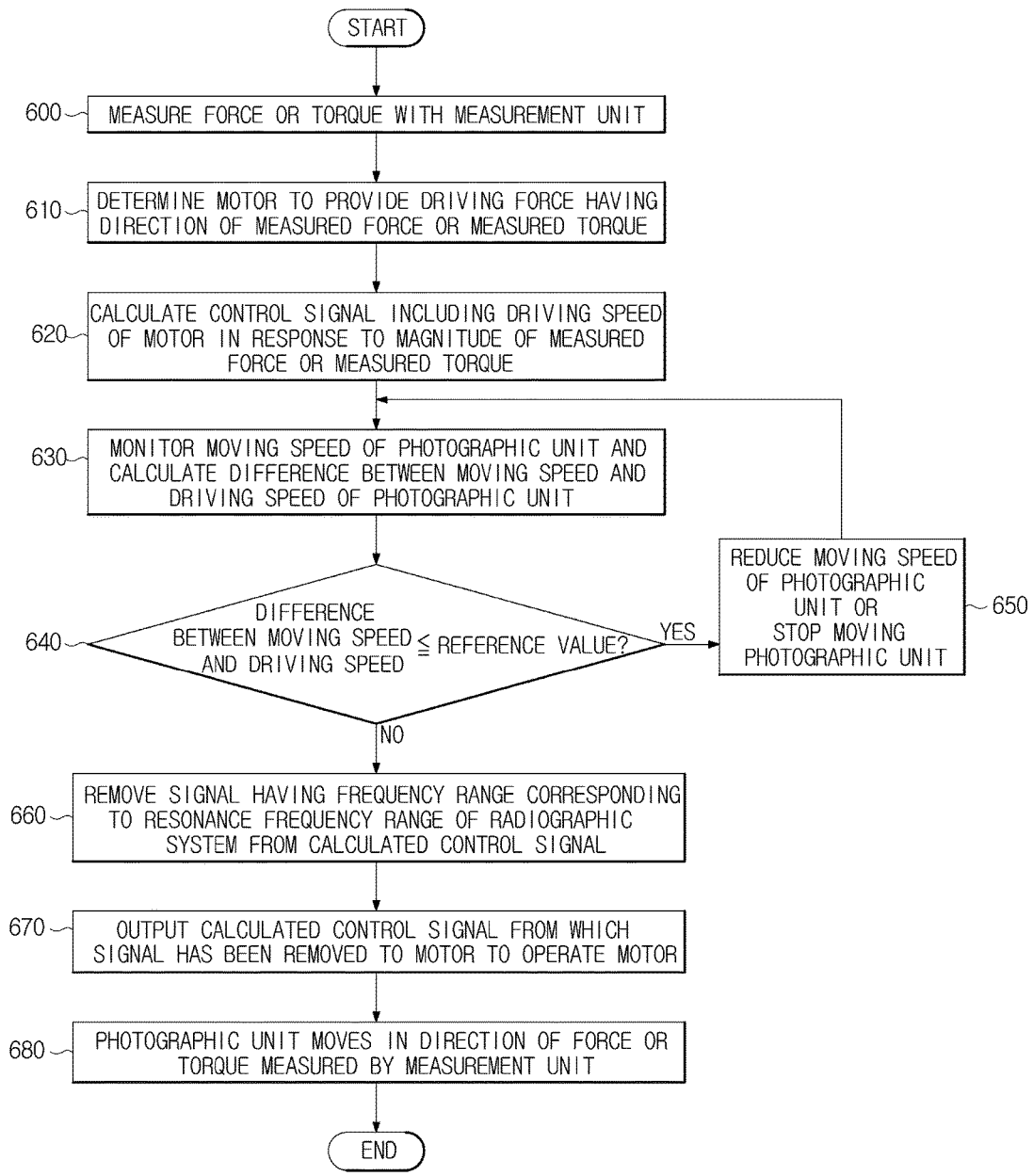
FIG. 21 is a flowchart illustrating a method of controlling the radiographic system of FIGS. 1-14 in accordance with one example.

FIG. 21 is a flowchart illustrating a method of controlling the radiographic system of FIGS. 1-14 in accordance with one example. Referring to FIG. 21, a force or a torque applied to the photographic unit 70 is measured by the measurement unit 126 (600) as described above in connection with FIGS. 1-14.

After the measurement unit 126 measures the force or the torque applied to the photographic unit 70, the system control unit 41 determines a motor of the motors 111, 112, 113, 114, and 115 of the motor unit 110 capable of providing a driving force in a direction of the measured force or the measured torque (610) as described above in connection with FIG. 14.

After the motor of the motor unit 110 is determined, the system control unit 41 calculates a control signal including a driving speed of the determined motor of the motor unit 110 based on the measured force or the measured torque (620) as described above in connection with FIG. 14. In one example, the system control unit 41 is capable of calculating control signals to control two or more of the motors 111, 112, and 113 simultaneously to move the photographic unit 70 (X-ray source unit) in two or more of the directions D1, D2, and D3 simultaneously if forces in two or more of the three directions intersecting one another (X-axis force, Y-axis force, and Z-axis force) are simultaneously sensed by the measurement unit 126 (sensor unit).

The system control unit 41 monitors a moving speed of the photographic unit 70, and calculates a difference between the moving speed of the photographic unit 70 and the driving speed of the photographic unit (630) as described above in connection with FIG. 14, determines whether the difference equals or exceeds a predetermined reference value (640) as described above in connection with FIG. 14, and reduces the moving speed of the photographic unit 70 or stops moving the photographic unit 70 if the difference equals or exceeds the predetermined reference value (650) as described above in connection with FIG. 14.

If the difference between the moving speed of the photographic unit 70 and the driving speed of the photographic unit 70 is smaller than the predetermined reference value, the control unit removes a signal having a frequency range corresponding to a resonance frequency range of the radiographic system from the calculated control signal including the driving speed of the determined motor of the motor unit 110 (660) as described above in connection with FIG. 14.

The system control unit 41 outputs the calculated control signal from which the signal having the frequency range corresponding to the resonance frequency range of the radiography apparatus has been removed to the determined motor of the motor unit 110 to operate the determined motor of the motor unit 110 (670) as described above in connection with FIG. 14, and as the determined motor of the motor unit 110 operates according to the control signal of the system control unit 41, the photographic unit 70 moves in the direction of the force or the torque measured by the measurement unit 126 (680) as described above in connection with FIG. 14.

Figure 22:
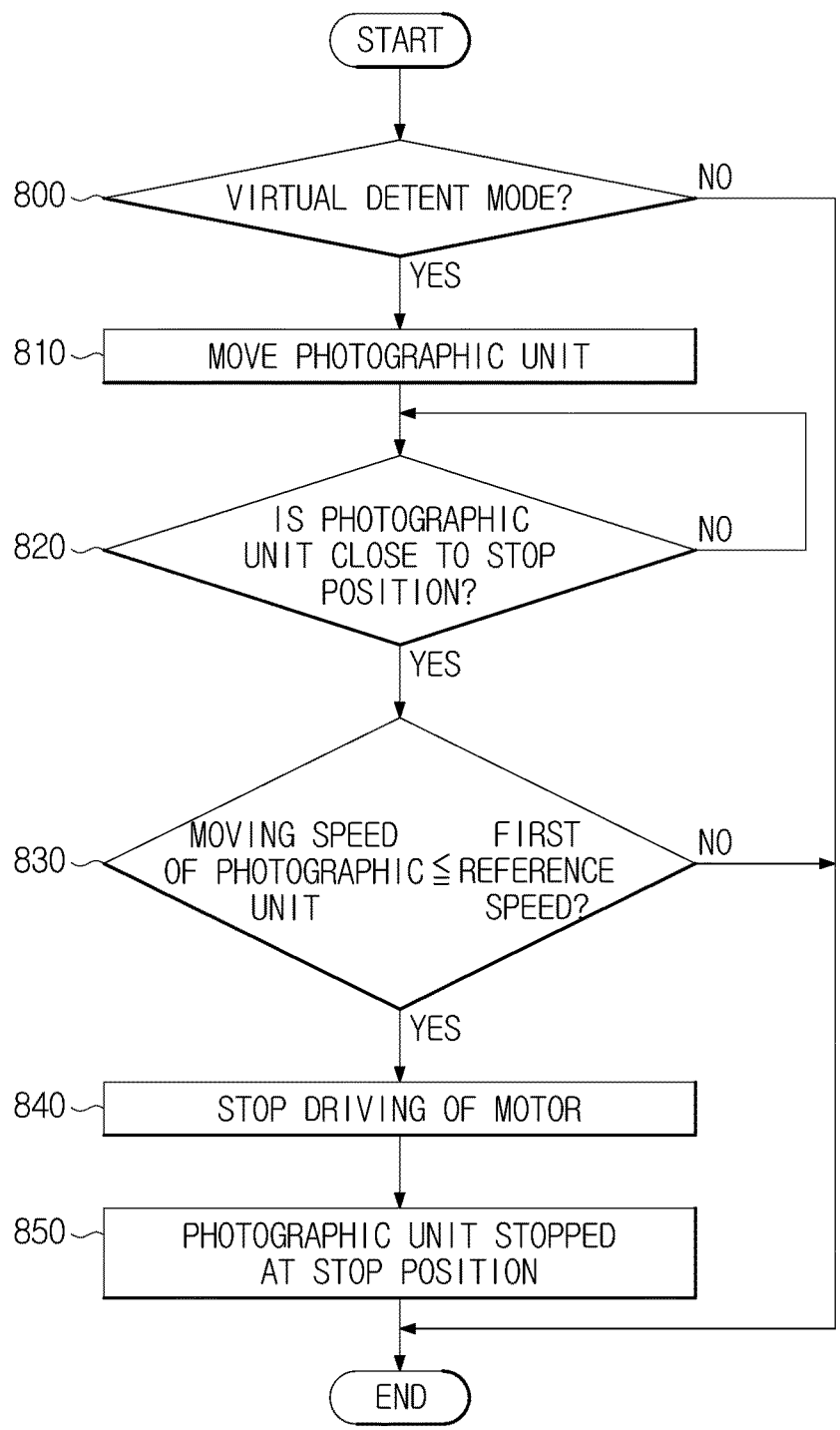
FIG. 22 is a flowchart illustrating a virtual detent mode of the radiographic system in accordance with one example.

FIG. 22 is a flowchart illustrating a virtual detent mode of the radiographic system in accordance with one example.

Referring to FIG. 22, the system control unit 41 determines whether an operating mode is the virtual detent mode (800).

An input unit such as a button provided on the manipulating unit (operating panel) 80 or the workstation to turn on and off the virtual detent mode if necessary is manipulated, and it is determined whether the virtual detent mode is turned on.

When the virtual detent mode is has been turned on and the photographic unit 70 moves (810), the system control unit 41 determines whether the photographic unit 70 is close to a stop position (820). When the photographic unit 70 is close to the stop position, the system control unit 41 determines whether the moving speed of the photographic unit 70 is less than or equal to the first reference speed (830). When the moving speed of the photographic unit 70 is less than or equal to the first reference speed, the system control unit 41 stops the driving of the motor (840), and the movement of the photographic unit 70 is stopped at the stop position (850).

The stop position at which the movement of the photographic unit 70 automatically stops in the virtual detent mode may be directly designated and set by the operator, and may be preset and stored as a position at which the photographic unit 70 is frequently located. For example, the position at which the photographic unit 70 is located may be a home position at which the photographic unit 70 is located while the radiographic system is not being used. The encoder or the potentiometer described above detects a position of the photographic unit 70 in real time and transmits the detected position to the system control unit 41, and the system control unit 41 determines whether the position of the photographic unit 70 detected in real time is equal to the stop position.

In addition, the speed sensor described above for detecting the moving speed of the photographic unit 70 detects the moving speed of the photographic unit 70 in real time and transmits the detected moving speed to the system control unit 41. The system control unit 41 determines whether the moving speed of the photographic unit 70 detected in real time is less than or equal to the preset first reference speed at the stop position. When the position of the photographic unit 70 is equal to the stop position and the moving speed of the photographic unit 70 is less than or equal to the first reference speed, the system control unit 41 causes the photographic unit 70 to stop at the stop position by stopping the driving of the motor that is assisting with the movement of the photographic unit 70.

Alternatively, the system control unit 41 may determine whether the position of the photographic unit 70 detected in real time and transmitted from the encoder or the potentiometer has entered a stop space having a predetermined volume including the stop position. In addition, when the position of the photographic unit 70 has entered the stop space, the system control unit 41 determines whether the moving speed of the photographic unit 70 determined in real time is less than or equal to the first reference speed, and gradually reducing the moving speed of the photographic unit 70 so that the photographic unit 70 may stop at the stop position when the moving speed of the photographic unit 70 is less than or equal to the first reference speed. Because it is possible to stop the photographic unit 70 by gradually reducing the moving speed of the photographic unit 70 without immediately stopping the photographic unit 70 by setting the stop space, the photographic unit 70 may more smoothly stop at the stop position.

The virtual detent mode has an advantage in that noise or vibration of the radiographic system due to using a brake to stop the movement of the photographic unit 70 may be prevented from occurring because the movement of the photographic unit 70 is stopped by stopping the driving of the motor without using the brake. Furthermore, the brake itself may be omitted as described above.

Figure 23:
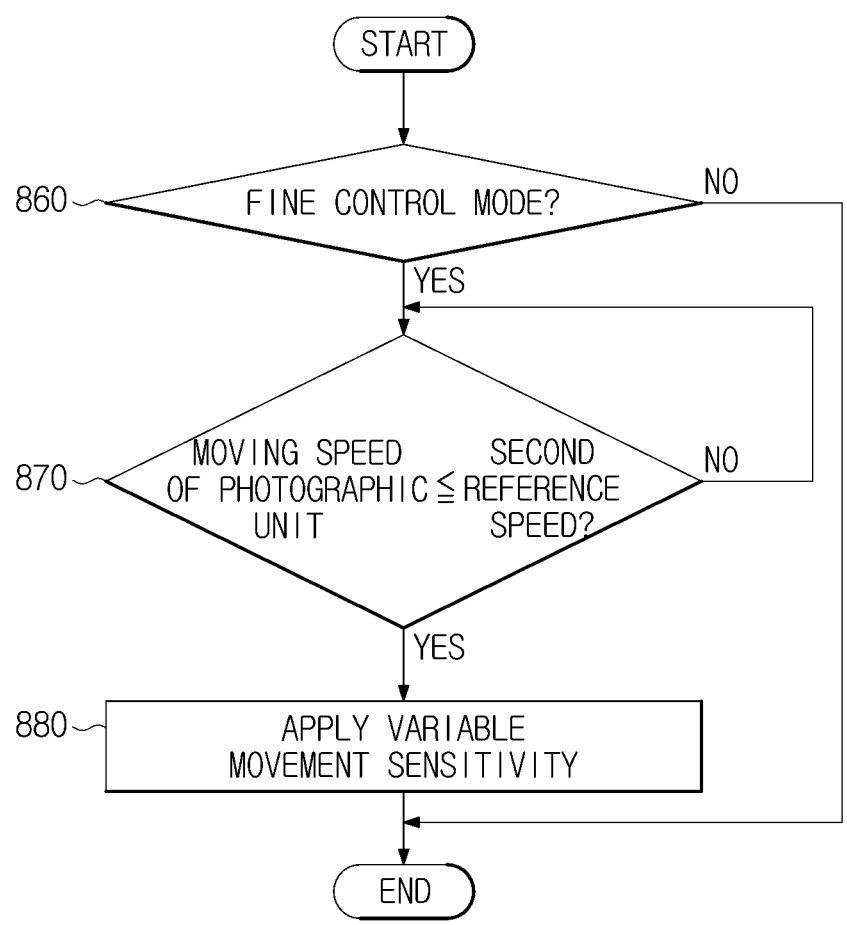
FIG. 23 is a flowchart illustrating a fine control mode of the radiographic system in accordance with one example.

FIG. 23 is a flowchart illustrating a fine control mode of the radiographic system in accordance with one example.

Referring to FIG. 23, the system control unit 41 determines whether the operating mode is the fine control mode (860).

An input unit such as a button provided on the operating panel 80 or the workstation to turn on and off the setting of the fine control mode if necessary is manipulated, and it is determined whether the fine control mode in which a variable movement sensitivity has been set is turned on.

When the fine control mode has been turned on, the system control unit 41 determines whether the moving speed of the photographic unit 70 is less than or equal to the second reference speed (870), and applies the variable movement sensitivity when the moving speed of the photographic unit 70 is less than or equal to the second reference speed (880).

As illustrated in FIG. 20, the movement sensitivity of the photographic unit 70 is fixed to a constant value when the moving speed of the photographic unit 70 is greater than the preset second reference speed, thereby providing a setting advantageous for the movement of the photographic unit 70. When the moving speed of the photographic unit 70 is less than or equal to the preset second reference speed, the movement sensitivity of the photographic unit 70 is set to be reduced as the moving speed of the photographic unit 70 is reduced, thereby providing a setting advantageous for the fine control of the photographic unit 70.

When the moving speed of the photographic unit 70 is less than or equal to the second reference speed, the movement sensitivity of the photographic unit 70 is reduced as the moving speed of the photographic unit 70 is reduced, and the operator may control the movement of the photographic unit 70 according to the operator's intention. For example, because a movement sensitivity (a) in FIG. 20 when the photographic unit 70 is being moved at a slow speed during fine control is less than a movement sensitivity (b) in FIG. 20 when the photographic unit 70 is being moved at a slightly faster speed during fine control, the operator may control the position of the photographic unit 70 with a higher precision than when the movement sensitivity value is fixed as in FIG. 19 even when the movement sensitivity value of the photographic unit 70 is small.

When the variable movement sensitivity has been set, the speed sensor detects the moving speed of the photographic unit 70 in real time and transmits the detected moving speed to the system control unit 41. The system control unit 41 controls the movement sensitivity according to a speed change of the photographic unit 70 as illustrated in FIG. 20 when the detected moving speed of the photographic unit 70 is less than or equal to the second reference speed.

Figure 24:
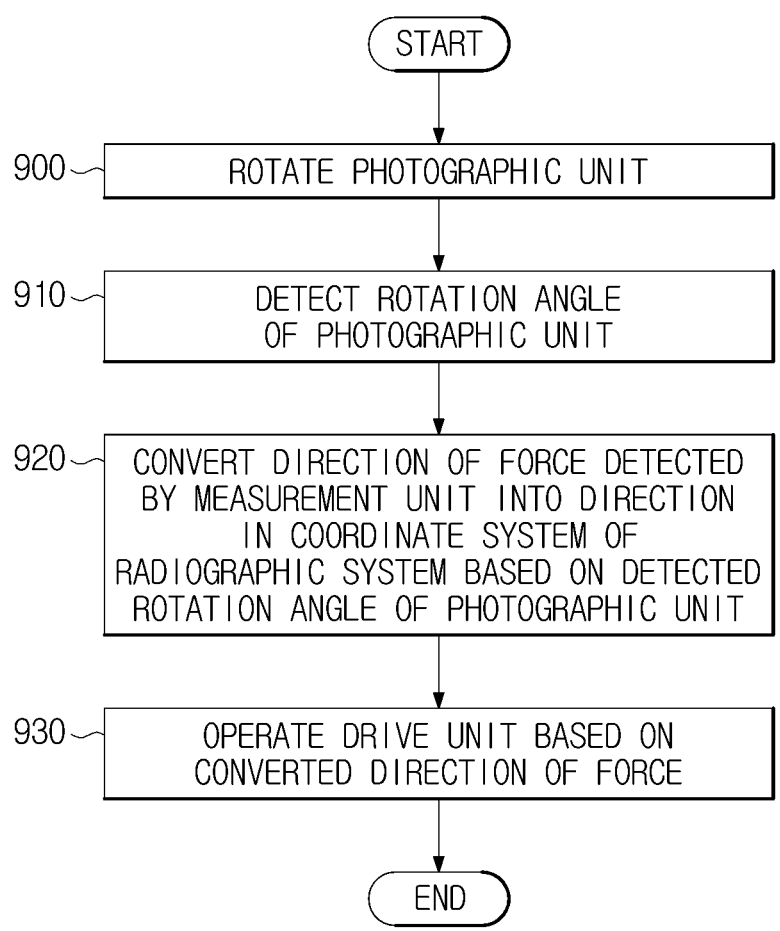
FIG. 24 is a flowchart illustrating a method of performing conversion from the coordinate system of the measuring unit to the coordinate system of the radiographic system in accordance with one example.

FIG. 24 is a flowchart illustrating a method of performing conversion from the coordinate system of the measuring unit 126 to the coordinate system of the radiographic system in accordance with one example.

Referring to FIG. 24, when the photographic unit 70 rotates (900), the encoder or the potentiometer of the motor rotating the photographic unit 70 detects a rotation angle of the photographic unit 70 (910). The system control unit converts a direction of a force detected by the measurement unit a direction in the coordinate system of the radiographic system based on the detected rotation angle of the photographic unit (920). The system control unit operates the drive unit based on the converted direction of the force (930).

As described above with respect to FIG. 16, an encoder or potentiometer measures the rotation angle of the photographic unit 70 in real time when the photographic unit 70 rotates in the fourth direction D4 or the fifth direction D5 measures the rotation angle of the photographic unit 70 and outputs the measured rotation angle to the system control unit 41. The system control unit 41 converts a force measured in the coordinate system of the measurement unit 126 to a force in the coordinate system of the radiographic system using the measured rotation angle output from the encoder or the potentiometer and the coordinate conversion defined by Equation 1.

That is, when the operator applies a force in the first or X-axis direction of the coordinate system of the radiographic system to move the photographic unit 70 in the first or X-axis direction in a state in which the photographic unit 70 has been rotated in the fourth direction D4 and the measurement unit 126 detects a direction of the force applied to the photographic unit 70 in the coordinate system of the measurement unit 126, the system control unit 41 converts a force measured in the coordinate system of the measurement unit 126 to a force in the coordinate system of the radiographic system using the rotation angle measured by the potentiometer or encoder and the coordinate conversion defined by Equation 1. When the force measured by the measurement unit 126 is converted to the force in the coordinate system of the radiographic system through the coordinate conversion, the system control unit 41 drives the motor for providing the driving force for moving the photographic unit 70 in the first or X-axis direction in place of the second or Y-axis direction and assist the operator with moving the photographic unit 70 in the first or X-axis direction.

The system control unit 41, the manipulating unit 80, the motor driver 100, the measurement unit or force/torque sensor 126, the firmware 133, the USART 134, and the RS-232 driver 135 described above that perform the various operations described above may be implemented using one or more hardware components, one or more software components, or a combination of one or more hardware components and one or more software components.

A hardware component may be, for example, a physical device that physically performs one or more operations, but is not limited thereto. Examples of hardware components include amplifiers, differential amplifiers, operational amplifiers, low-pass filters, high-pass filters, band-pass filters, analog-to-digital converters, digital-to-analog converters, registers, differentiators, comparators, arithmetic units, functional units, memory devices, radio cards, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A radiographic system comprising:
a radiographic device configured to be movable;
a handle coupled to the radiographic device, the handle comprising a switch configured to be pressed and released by an operator;
an operating panel assembly coupled to the radiographic device so that the operating panel assembly is movable with the radiographic device, the operating panel assembly comprising a display screen configured to display a captured image; and
a driver configured to operate in a power-assisted mode in which a movement of the radiographic device is power-assisted according to a physical force applied to the handle;
wherein pressing of the switch turns on the power-assisted mode of the driver, and releasing of the switch turns off the power-assisted mode of the driver.

2. The radiographic system of claim 1, wherein the display screen comprises a touch screen configured to receive a touch input of radiographic information for operating the radiographic device.

3. The radiographic system of claim 1, wherein the captured image comprises an image produced by the radiographic device.

4. The radiographic system of claim 1, wherein the radiographic device comprises an X-ray device; and
the captured image comprises an X-ray image produced by the X-ray device.

5. The radiographic system of claim 1, wherein the captured image is a current captured image; and
the display screen is further configured to display the current captured image immediately after the current captured image has been captured.

6. The radiographic system of claim 1, wherein the driver is further configured to selectively move the radiographic device in the power-assisted mode according to the physical force applied to the handle, and move the radiographic device in response to the operator inputting an instruction.

7. The radiographic system of claim 6, further comprising a measuring device configured to measure the physical force applied to the handle;
wherein the driver is further configured to move the radiographic device in the power-assisted mode according to the physical force applied to the handle based on the physical force measured by the measuring device.

8. The radiographic system of claim 6, wherein the operating panel assembly is configured to enable the operator to apply the physical force to the handle to control the movement of the radiographic device in the power-assisted mode; and
the display screen is further configured to display the captured image in the power-assisted mode.

9. The radiography system of claim 1, wherein the driver is further configured to respond to the releasing of the switch by enabling movement of the radiographic device in response to the radiography system receiving an instruction designating a position to which the radiographic device is to move.

10. A radiographic system comprising:
a radiographic device configured to be movable;
a handle coupled to the radiographic device, the handle comprising a switch configured to be pressed and released by an operator;
an operating panel assembly coupled to the radiographic device so that the operating panel assembly is movable with the radiographic device, the operating panel assembly comprising a display screen configured to display a captured image; and
a driver configured to selectively move the radiographic device in response to the operator inputting an instruction, and operate in a power-assisted mode in which a movement of the radiographic device is power-assisted according to a physical force applied to the handle;
wherein pressing of the switch turns on the power-assisted mode of the driver, and releasing of the switch turns off the power-assisted mode of the driver.

11. The radiographic system of claim 10, wherein the display screen comprises a touch screen configured to receive a touch input of radiographic information for operating the radiographic device.

12. The radiographic system of claim 10, wherein the captured image comprises an image produced by the radiographic device.

13. The radiographic system of claim 10, wherein the radiographic device comprises an X-ray device; and
the captured image comprises an X-ray image produced by the X-ray device.

14. The radiographic system of claim 10, wherein the captured image is a current captured image; and
the display screen is further configured to display the current captured image immediately after the current captured image has been captured.

15. The radiographic system of claim 10, wherein the operating panel assembly is configured to enable the operator to apply the physical force to the handle to control the movement of the radiographic device in the power-assisted mode; and
the display screen is further configured to display the captured image in the power-assisted mode.

16. The radiographic system of claim 10, further comprising a measuring device disposed between the radiographic device and the operating panel assembly, and configured to measure the physical force applied to the handle;
wherein the driver is further configured to move the radiographic device in the power-assisted mode according to the physical force applied to the handle based on the physical force measured by the measuring device.

17. The radiography system of claim 10, wherein the instruction designates a position to which the radiographic device is to move; and
the driver is further configured to respond to the releasing of the switch by enabling movement of the radiographic device in response to the radiography system receiving the instruction designating the position to which the radiographic device is to move.

18. A radiographic system comprising:
a radiographic device configured to be movable;
an operating panel assembly coupled to the radiographic device so that the operating panel assembly is movable with the radiographic device, the operating panel assembly comprising a display screen configured to display a captured image;

a driver configured to move the radiographic device based on a direction and a magnitude of an external force applied to the operating panel assembly; and a measuring device disposed between the radiographic device and the operating panel assembly, and configured to measure the direction and the magnitude of the external force applied to the operating panel assembly;

wherein the driver is further configured to move the radiographic device based on the direction and the magnitude of the external force measured by the measuring device.

* * * * *